(12) United States Patent
Stokes

(10) Patent No.: US 12,403,139 B2
(45) Date of Patent: *Sep. 2, 2025

(54) METHODS AND COMPOSITIONS FOR PREVENTION AND TREATMENT OF CARDIAC HYPERTROPHY

(71) Applicant: University of Hawaii, Honolulu, HI (US)

(72) Inventor: Alexander Stokes, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/243,572

(22) Filed: Sep. 7, 2023

(65) Prior Publication Data
US 2024/0189303 A1 Jun. 13, 2024

Related U.S. Application Data

(60) Continuation of application No. 16/928,967, filed on Jul. 14, 2020, now abandoned, which is a continuation of application No. 16/181,204, filed on Nov. 5, 2018, now abandoned, which is a continuation of application No. 15/583,867, filed on May 1, 2017, now Pat. No. 10,137,123, which is a continuation of application No. 14/745,060, filed on Jun. 19, 2015, now abandoned, which is a division of application No. 13/824,912, filed as application No. PCT/US2011/058967 on Nov. 2, 2011, now Pat. No. 9,084,786.

(60) Provisional application No. 61/409,781, filed on Nov. 3, 2010.

(51) Int. Cl.
*A61K 31/496* (2006.01)
*A61K 31/00* (2006.01)
*A61K 31/497* (2006.01)
*A61P 9/04* (2006.01)

(52) U.S. Cl.
CPC ............ *A61K 31/496* (2013.01); *A61K 31/00* (2013.01); *A61K 31/497* (2013.01); *A61P 9/04* (2018.01)

(58) Field of Classification Search
CPC .................................................... A61K 31/496
See application file for complete search history.

(56) References Cited

U.S. PATENT DOCUMENTS

| | | | |
|---|---|---|---|
| 9,084,786 B2 * | 7/2015 | Stokes | A61K 31/497 |
| 10,137,123 B2 * | 11/2018 | Stokes | A61P 9/04 |
| 2007/0135423 A1 | 6/2007 | Bayliss et al. | |
| 2008/0058401 A1 | 3/2008 | Lee et al. | |
| 2008/0214574 A1 | 9/2008 | Gram et al. | |
| 2008/0234383 A1 | 9/2008 | Suh et al. | |
| 2008/0269253 A1 | 10/2008 | Gharat et al. | |

FOREIGN PATENT DOCUMENTS

WO   WO 2005049084 A2   6/2005

OTHER PUBLICATIONS

Benko, Rita, et al. "Use and limitations of three TRPV-1 receptor antagonists on smooth muscles of animals and man: A vote for BCTC", European Journal of Pharmacology (2012) 674, 44-50.
Buckley, C. L. et al., "Mice lacking functional TRPV1 are protected from pressure overload cardiac hypertrophy", Channels (2011) 5:4, 1-8.
Caterina, M. J. et al. "Impaired nociception and pain sensation in mice lacking the capsaicin receptor. Science", (2000) 288:306-313.
Communication pursuant to Article 94(3) EPC received in EP Application No. 18 154 283.8-1109, mailed Oct. 23, 2019.
Examination Report received in Indian Application No. 1404/KOLNP/2013, dated May 30, 2018.
Extended European Search Report received in European Application No. 18154283.8, dated May 30, 2018.
Gergs, et al. "Overexpression of the Catalytic Subunit of Protein Phosphatase 2A Impairs Cardiac Function", The Journal of Biological Chemistry 279(39):40827-40834 (2004).
Goadsby, et al., "Emerging therapies for migraine," Nature Clinical Practice Neurology, Nature Publishing Group, London, GB, vol. 3, No. 11, Jan. 1, 2007, pp. 610-619.
Gunthorpe, M. J., et al. "Discovery of novel 6, 6-heterocycles as transient receptor potential vanilloid (TRPV1) antagonists", Neuropharmacol. (2004) 46(1):133-49.
Gunthorpe, Martin J., et al. "Characterization of SB-705498, a Potent and Selective Vanilloid Receptor-1 (VR1/TRPV1) Antagonist That Inhibits the Capsaicin-, Acid-, and Heat- Mediated Activation of the Receptor", The Journal of Pharmacology and Experimental Therapeutics, 2007, vol. 321, No. 3, 1183-1192.
Horton, Jaime S. et al., "Successful TRPV1 antagonist treatment for cardiac hypertrophy and heart failure in mice," Channels 7 (1), pp. 17-22.
Huang W. et al., "Transient receptor potential vanilloid gene deletion exacerbates inflammation and atypical cardiac remodeling after myocardial infraction," Hypertension vol. 53, No. 2, Feb. 2009, pp. 243-250.
Hunt et al., ACC/AHA 2005 Guideline Update for the Diagnosis and Management of Chronic Heart Failure in the Adult: A Report of the American College of Cardiology/American Heart Association Task Force on Practice Guidelines (Writing Committee to Update the 2001 Guidelines for the Evaluation and Management of Heart Failure), Journal of the American C.

(Continued)

*Primary Examiner* — Svetlana M Ivanova
(74) *Attorney, Agent, or Firm* — Knobbe, Martens, Olson & Bear LLP

(57) ABSTRACT

Methods are provided of treating cardiac hypertrophy in a mammalian subject comprising administering to the subject an anti-hypertrophic effective amount of an ion channel TR-PV1 inhibitor. The methods include treatment of a symptom of cardiac hypertrophy in the subject comprises cardiac remodeling, cardiac fibrosis, apoptosis, hypertension, or heart failure.

11 Claims, 11 Drawing Sheets

(56) References Cited

OTHER PUBLICATIONS

Inoue R. et al., "Mechanosensitive TRP channels in cardiovascular pathophysiology," Pharmacology and Therapeutics, Elsevier, GB, vol. 123, No. 3, Sep. 1, 2009, pp. 371-385.
Kym, Philip R., et al. "Analgesic potential of TRPV1 antagonists", Biochemical Pharmacology (2009), 78, 211-216.
Lin, Z. et al. "Nobilamides A-H, long-acting transient receptor potential vanilloid-1 (TRPV1) antagonists from mollusk-associated bacteria", J. Med. Chem. (2011) 54(11):3746-55.
Liu, L. et al. "Capsazepine, a vanilloid receptor antagonist, inhibits nicotinic acetylcholine receptors in rat trigeminal ganglia", Neuroscience Letters (1997), 228, 29-32.
Lu, Songhe, et al. "Cold stress accentuates pressure overload-induced cardiac hypertrophy and contractile dysfunction: Role of TRPV1/AMPK-mediated autophagy", Biochemical and Biophysical Research Communities (2013) 442, 8-15.
Lygate, C. "Surgical models of hypertrophy and heart failure: Myocardial infarction and transverse aortic constriction", Drug Discovery Today: Disease Models (2006) 3:283-290.
Mathie A. "Ion channels as novel therapeutic targets in the treatment of pain," Journal of Pharmacy and Pharmacology 2010 Pharmaceutical Press, GBR, vol. 62, No. 9, Sep. 9, 2010, pp. 1089-1095.
Messeguer, A., et al. "Physiology and pharmacology of the vanilloid receptor", Curr. Neuropharmacol. (2006) 4(1):1-15.
Moran, Magdalene M., et al., "Transient receptor potential channels as therapeutic targets", Nature Reviews Drug Discovery, Aug. 2011, vol. 10, 601-620.
Nilius, Bernd, et al. "Transient Receptor Potential Channels as Drug Targets: From the Science of Basic Research to the Art of Medicine", Pharmacol Rev Jul. 2014, 66:676-814.
Notice of Reexamination issued in Chinese application No. 201180063998.4 on Nov. 1, 2016.
Patten, R. D., et al. "Small animal models of heart failure: development of novel therapies, past and present", Circ Heart Fail (2009) 2:138-144.
Roberts, Louise A., et al. "TRPV1 Antagonists as a Potential Treatment for Hyperalgesia", Recent Patents on CNS Drug Discovery, (2006), 1, 65-76.
Rockman, H. A., et al., "Molecular and physiological alterations in murine ventricular dysfunction", Proc Natl Acad Sci USA (1994) 91:2694-2698.
Rockman, H. A., et al., "Segregation of atrial-specific and inducible expression of an atrial natriuretic factor transgene in an in vivo murine model of cardiac hypertrophy", Proc Natl Acad Sci USA (1991) 88:8277-8281

Shiojima, I., et al. "Disruption of coordinated cardiac hypertrophy and angiogenesis contributes to the transition to heart failure", J. Clin. Invest. (2005) 115:2108-18.
Smith, Scott A., et al. "The Capsaicin-Sensitive Afferent Neuron in Skeletal Muscle is Abnormal in Heart Failure", Circulation (2005) 111, 2056-2065.
Thilo, et al. "Increased transient receptor potential vanilloid type 1 (TRPV1) channel expression in hypertrophic heart", Biochemical and Biophysical Research Communications 401 (2010) 98-103, available online Sep. 15, 2010.
Trevisani, Marcello, et al. "Targeting TRPV1: Challenges and Issues in Pain Management", The Open Drug Discovery Journal, 2010, 2, 37-49.
Trevisani, Marcello, et al. "TRPV1 Antagonists as Analgesic Agents", The Open Pain Journal, 2013, 6, (Suppl 1:M11) 108-118.
Tsareva, Daria A., et al. "How Far Could We Go with Open Data—A Case Study for TRPV1 Antagonists", Molecular Informatics, DOI: 10.1002.
Varga, Angelika, et al. "Effects of the novel TRPV1 receptor antagonist SB366791 in vitro and in vivo in the rat", Neuroscience Letters 2005, 385, 137-142.
Wang, Han-Jun, et al. "Cardiac Sympathetic Afferent Denervation Attenuates Cardiac Remodeling and Improves Cardiovascular Dysfunction in Rats with Heart Failure", Hypertension, (2014); 64:747-755.
Wang, Han-Jun, et al. "Alteration in skeletal muscle afferents in rats with chronic heart failure", Journal of Physiology (2010) vol. 588, No. 24, 5033-5047.
Wang, Youping et al. "Endocannabinoid Regulates Blood Pressure via Activation of the Transient Receptor Potential Vanilloid Type 1 in Wistar Rats Fed a High-Salt Diet", The Journal of Pharmacology and Experimental Therapeutics, (2007) 321:763:-769.
Wang, Yun, et al. "High Affinity Antagonists of the Vanilloid Receptor", Molecular Pharmacology (2002) 62:947-956.
Wang et al., TRPV1 Gene Knockout Impairs Postischemic Recovery in Isolated Perfused Heart in Mice, Circulation. 2005;112:3617-3623.
Zhong Beihua et al., "Ablation of TRPV1 Exacerbates Pressure Overload-Induced Cardiac Hypertrophy," Circulation, vol. 118, No. 18, Suppl., Oct. 2, 2008, p. S546.
Beevers, Gareth et al., "ABC of Hypertension The Pathophysiology of Hypertension", BMJ, Apr. 14, 2001, vol. 322, pp. 912-916.
Mathie A. "Ion channels as novel therapeutic targets in the treatment of pain," Journal of Pharmacy and Pharmacology 2010 Pharmaceutical Press, GBR, vol. 62, No. 9, Sep. 9, 2010, pp. 1089-1095.
Shiojima, L., et al. "Disruption of coordinated cardiac hypertrophy and angiogenesis contributes to the transition to heart failure", J. Clin. Invest. (2005) 115:2108-18.
Zhong Beihua et al., "Ablation of TRPV1 Exacerbates Pressure Overload-Induced Cardiac Hypertrophy," Circulation, vol. 118, No. 18, Suppl., Oct. 2, 2008, page S546.

* cited by examiner

METHODS AND COMPOSITIONS FOR PREVENTION AND TREATMENT OF CARDIAC HYPERTROPHY

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/928,967, filed on Jul. 14, 2020, which is a continuation of U.S. application Ser. No. 16/181,204, filed Nov. 5, 2018, which is a continuation of U.S. application Ser. No. 15/583,867, filed on May 1, 2017, now U.S. Pat. No. 10,137,123, which is a continuation of U.S. application Ser. No. 14/745,060, filed on Jun. 19, 2015, now abandoned, which is a divisional of U.S. application Ser. No. 13/824,912, filed on Mar. 18, 2013, now U.S. Pat. No. 9,084,786, which is the national phase under 35 U.S.C. § 371 of prior PCT International Application No. PCT/US11/58967 which has an International filing date of Nov. 2, 2011, which claims priority under 35 U.S.C. § 119 (e) to U.S. provisional application Ser. No. 61/409,781, filed on Nov. 3, 2010. Each of the aforementioned applications is incorporated by reference herein in its entirety, and each is hereby expressly made a part of this specification.

U.S. GOVERNMENT RIGHTS

This invention was made with government support under grant numbers U54 RR026136, P20 RR016467, P20 MD006084, and P20 RR016453 awarded by the National Institutes of Health. The government has certain rights in the invention.

REFERENCE TO SEQUENCE LISTING

The present application incorporates by reference the sequence listing submitted as an ASCII text filed via EFS-Web on May 1, 2017.

FIELD OF THE INVENTION

The present invention relates to the treatment and prevention cardiac hypertrophy. More specifically, the invention relates to methods and compositions for preventing or treating cardiac hypertrophy, cardiac remodeling, fibrosis, hypertension, and heart failure in mammals, including humans, through inhibition of the ion channel TRPV1.

BACKGROUND

Myocardial hypertrophy is the fundamental response of the heart to a chronically increased workload, which can result from conditions such as hypertension or valve disorders. The progression of myocardial hypertrophy represents a principal risk factor for the development of heart failure and subsequent cardiac death.

The focus of this invention is on combating hypertrophy, apoptosis fibrosis, and heart failure, focuses on regulation of TRPV1 (transient receptor potential cation channel, subfamily V, member 1), a complex and remarkable receptor/channel. TRPV1 is typically classified as a nociceptive receptor. Published data indicate that the open probability of TRPV1 is controlled by the endocannabinoid anandamide, its endogenous ligand, and pathways modulating anandamide levels also influence TRPV1 activation. The etiology of hypertrophic regulation by TRPV1 (transient receptor potential cation channel, subfamily V, member 1) is unknown. There is only a general understanding of how TRPV1 is regulated, and of the identity of several cell and tissue types in which TRPV1 resides.

TRPV1 has been studied in peripheral sensory neurons as a pain receptor; however TRPV1 is expressed in numerous tissues and cell types including those of the cardiovascular system. TRPV1 expression is upregulated in the hypertrophic heart, and the channel is positioned to receive stimulatory signals in the hypertrophic heart. TRPV1 is a six trans-membrane tetrameric nonselective cation channel, typically associated with peripheral sensory neurons involved in nociception. Exogenous activators of TRPV1 include temperature of greater than 43° C. and capsaicin. Endogenously, TRPV1 is activated and potentiated by the endocannabinoids, anandamide and N-arachidonoyl-dopamine, low pH, and phosphorylation by protein kinase C (PKC) and cyclic AMP-dependent protein kinase (PKA). The nociceptive involvement of TRPV1 activation in peripheral sensory neurons has prompted substantial study of TRPV1 as a target for inhibition. Consequently a plethora of effective TRPV1 antagonists has been produced and demonstrated to be effective analgesics in the management of inflammatory pain and hyperalgesia.

In addition to the peripheral sensory neurons, TRPV1 is also found in other excitable and non-excitable tissues, including those of the heart and circulatory system. For example, cardiomyocytes, cardiac blood vessels, perivascular nerves, pulmonary artery smooth muscle cells, and coronary endothelial cells, skeletal muscle, mast cells, and dendritic cells express TRPV1.

Although TRPV1 inhibition has not been studied in the context of cardiac hypertrophy, TRPV1 activation has been implicated in protection from myocardial ischemia reperfusion injury. In addition, the channel's endogenous ligand, anandamide, has been implicated in multiple cardiac diseases such as cardiotoxicity and hypertension.

SUMMARY OF EXEMPLARY EMBODIMENTS OF THE INVENTION

The invention provides methods of treating cardiac hypertrophy in a mammalian subject comprising administering to the subject an anti-hypertrophic effective amount of an ion channel TRPV1 inhibitor. In some embodiments, the invention provides methods of treatment where a symptom of cardiac hypertrophy in the subject comprises cardiac remodeling, cardiac fibrosis, apoptosis, hypertension, or heart failure.

The invention further provides methods prophylactic treatment for cardiac hypertrophy in a mammalian subject comprising administering to the subject an anti-hypertrophic effective amount of an ion channel TRPV1 inhibitor.

The invention also provides pharmaceutical compositions comprising a pharmaceutically effective amount of an ion channel TRPV1 inhibitor or mixtures of such inhibitors useful for the methods of the invention.

The invention also provides pharmaceutical compositions comprising a pharmaceutically effective amount of the ion channel TRPV1 inhibitor (N-(4-t-butyl-phenyl)-4-(3-chloropyridin-2-yl)-tetrahydropyrazine-1(2H)-carboxamide or mixtures of that inhibitor with other ion channel TRPV1 inhibitors useful for the methods of the invention.

BRIEF DESCRIPTION OF THE FIGURES

FIGS. 1A-1D are graphs of results of data obtained by the procedures described in Example 1.

DETAILED DESCRIPTION EXEMPLARY EMBODIMENTS OF THE INVENTION

Figure 1D:
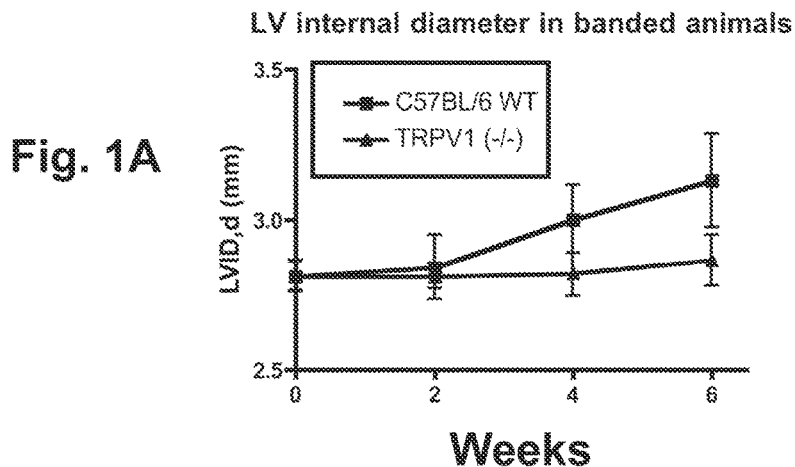
Figure 1D:
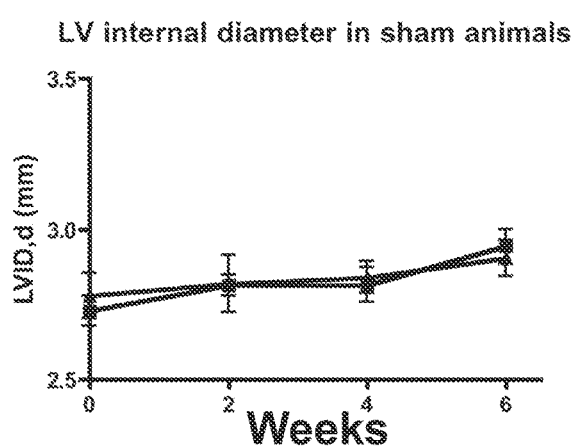
Figure 1D:
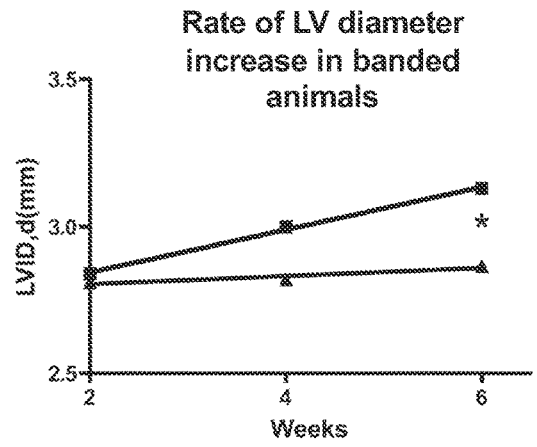
Figure 1D:
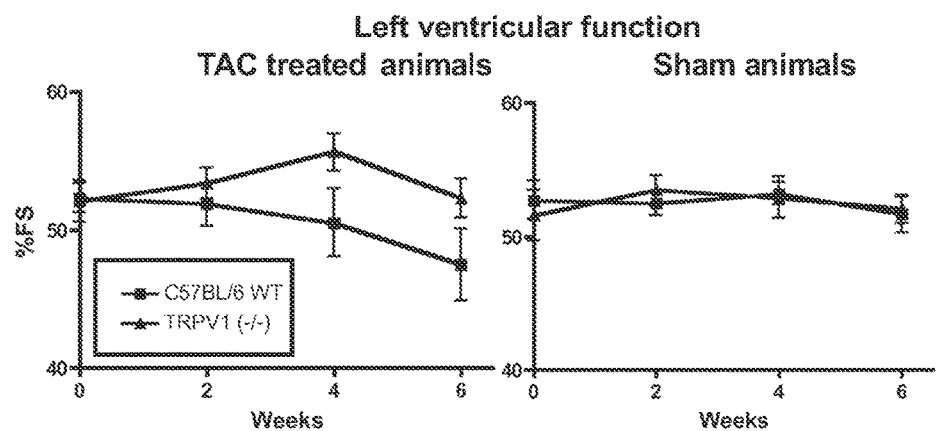

Cardiac hypertrophy is classically considered to be an adaptive and compensatory response that increases the work output of cardiomyocytes and thus maintains cardiac function despite increased load. In mice, cardiac hypertrophy is typically modeled using transverse aortic constriction (TAC) to induce acute pressure overload. The increased resistance created by aortic constriction initially compromises left ventricular (LV) function; the subsequent development of LV hypertrophy begins to restore systolic function in the two weeks following TAC. Concentric LV hypertrophy continues during weeks two to eleven post-TAC, potentially doubling the LV mass compared to controls. A decline in LV function accompanies LV chamber dilation and myocardial fibrosis, and around half of TAC treated mice develop pulmonary congestion by week eleven. Thus, TAC is an effective stimulus for rapidly producing cardiac hypertrophy in an experimental setting. The TAC model provides tremendous utility for identifying important therapeutic targets in heart disease and exploring the effects of molecular or pharmacological inhibitors.

This invention shows that TRPV1 function is a new target for protective therapy in cardiac hypertrophy, fibrosis and heart failure using TRPV1-directed therapeutics, this invention has the potential to shift clinical treatment paradigms for cardiac hypertrophy and heart failure by repurposing existing drugs.

As shown below in the examples the loss of TRPV1 function in mice alters the responses of the heart to TAC-induced pressure overload. TRPV1 contributes to cardiac hypertrophy, fibrosis, apoptosis, and loss of contractile function in response to pressure overload. TRPV1 antagonists previously known as anti-hyperalgesics are unexpectedly provided by the methods of the present invention as anti-hypertrophic agents.

As shown in the examples the knockout of Trpv1 significantly suppresses the ventricular enlargement, apoptosis, tissue remodeling and fibrosis associated with modeled pressure overload cardiac hypertrophy. This phenotype mirrors some of the most desirable effects for anti-hypertrophic treatments. By use of a transverse aortic constriction to model pressure overload cardiac hypertrophy mice lacking functional TRPV1, compared to wild type, have improved heart function, and reduced hypertrophic, fibrotic and apoptotic markers. TRPV1 plays a role in the progression of cardiac hypertrophy, and presents a therapeutic target for the treatment of cardiac hypertrophy and subsequent disease states including arrhythmias, kidney dysfunction and heart failure; treatment and alleviation of symptoms leading to cardiac hypertrophy and heart failure such as high blood pressure, heart valve disease, weakness of the heart muscle (cardiomyopathy), abnormal heartbeat, anemia, thyroid disorders, excessive drug use, muscular dystrophy and Fabry's disease, aortic valve stenosis, side effects of chemotherapy agents leading to toxic cardiomyopathy, obesity, diabetes, cigarette smoking, viral myocarditis (an infection of the heart muscle), infiltrations of the muscle such as amyloidosis, HIV cardiomyopathy (caused by human immunodeficiency virus), connective tissue diseases such as systemic lupus erythematosus, abuse of drugs such as alcohol and cocaine, and side effects of arrhythmias or pharmaceutical drugs such as chemotherapeutic agents.

In addition to the compounds and compositions having activity herein, other compounds having the requisite activity may be identified by the following test. Since cardiac hypertrophy is classically considered to be an adaptive and compensatory response that increases the work output of cardiomyocytes and thus maintains cardiac function despite increased load, the following test will identify a compound as having the activity useful in accordance with the invention. In mice, cardiac hypertrophy is typically modeled using transverse aortic constriction (TAC) to induce acute pressure overload. The increased resistance created by aortic constriction initially compromises left ventricular (LV) function; the subsequent development of LV hypertrophy begins to restore systolic function in the two weeks following TAC. Concentric LV hypertrophy continues during weeks two to eleven post TAC, potentially doubling the LV mass compared to controls. A decline in LV function accompanies LV chamber dilation and myocardial fibrosis, and around half of TAC treated mice develop pulmonary congestion by week eleven. Thus, TAC is an effective stimulus for rapidly producing cardiac hypertrophy in an experimental setting. Although there are differences between the TAC model and clinical cardiac hypertrophy, this model mimics the acute onset of hypertension rather than the gradual onset in clinical cases. However, the TAC model is useful for identifying important therapeutic targets in heart disease and exploring the effects of molecular or pharmacological inhibitors. (Lygate, 2006; Patten and Hall-Porter, 2009)

Test Model

Generation of the Model in the Mouse

Transverse Aortic Constriction (TAC). Transverse aortic constriction was performed as described by Rockman, producing left ventricular hypertrophy by constriction of the aorta (Rockman et al., 1994; Rockman et al., 1991). The left side of the chest was depilated with Nair and a baseline 2-D echocardiogram was obtained. Mice were then deeply anesthetized with a mixture of ketamine and xylazine. The transverse aorta between the brachiocephalic and left carotid artery was banded using 6-0 silk ligature around the vessel and a 26 G blunt needle, after which the needle was withdrawn. Sham surgeries were identical apart from the constriction of the aorta.

Checking for Successful Banding

Doppler echocardiography. Doppler echocardiography was performed one week post TAC to measure the level of constriction. Mice were anesthetized lightly with isofluorene gas and shaved. Doppler was performed using the Visualsonics Vevo 770 system. In the parasternal short-axis view, the pulsed wave Doppler sample volume was placed in the transverse aorta just proximal and distal to the site of banding. Peak velocity was traced using Vevo 770 software, and the pressure gradient was calculated using the simplified Bernoulli equation.

Following the Structural Changes in Heart Dimensions During the Progression of the Modeled Disease Transthoracic echocardiography. Baseline and post TAC transthoracic echocardiography were used to assess changes in mouse heart dimensions and function. Briefly, after two days of acclimatization and depilation, unanesthetized transthoracic echocardiography was performed using a 30-Mhz transducer (Vevo 770, VisualSonics). High quality two-dimensional images and M-mode images of the left ventricle were recorded. Measurements of left ventricular end-diastolic (LVIDd) and end-systolic (LVIDs) internal dimensions were performed by the leading edge to leading edge convention adopted by the American Society of Echocardiography. The left ventricular ejection fraction (% EF) was calculated as (LV Vol; d-LV Vol; s/LV Vol; d×100) (Visualsonics Inc.).

Testing the Degree of Cellular Hypertrophy, Fibrosis, and Apoptosis Post Treatment Markers of hypertrophy, fibrosis, tissue remodeling, inflammation and apoptosis, are assessed by either Western Blot (WB) analysis, real-time PCR of extracted RNA (RT), or histological and immunohistological analysis (H).

Hypertrophic markers can include: $ANP^{(WB, RT)}$, $BNP^{(RT)}$, $ACTA1^{(RT)}$, $\alpha\text{-MHC}^{(RT)}$, $\beta\text{-MHC}^{(RT)}$, $MLC2A^{(RT)}$, and Wheat-germ agglutinin$^{(H)}$ to generate cardiomyocyte cross sectional area.

Tissue remodeling markers can include: Chymase $CMA1^{(WB, RT)}$, $MMP\text{-}2^{(RT)}$, $MMP\text{-}9^{(RT)}$, $TGF\text{-}\beta^{(RT)}$, Collagen $III^{(RT,H)}$, fibrinogen$^{(RT, H)}$, Fibroblast proliferation $CD29^{(H)}$.

Apoptosis markers can include: Cleaved Caspase-3$^{(WB)}$.

Immunological, inflammatory and infiltration markers can include: $IL\text{-}6^{(RT)}$, $TNF\text{-}\alpha^{(RT)}$, $NOS3^{(RT)}$, CD68 (Macrophages)$^{(WB,RT,H)}$, histidine decarboxylase$^{(WB)}$ and Fc $R1\alpha^{(WB)}$ (Mast cells)$^{(WB,RT,H)}$, $CD4^+/CD8^+$ T-cell markers$^{(WB,H)}$, NK cell $CD161^{(RT,WB,H)}$ Tissue preparation for histology. Eight weeks post TAC, mice were euthanized by $CO_2$ asphyxiation, and hearts were collected for histological and molecular analysis. For histology, hearts were perfused with phosphate-buffered saline and 10% formalin in situ, collected immediately, and fixed overnight in 10% formalin at 4° C. Tissues were then cut in a sagittal orientation, embedded in paraffin, mounted on glass slides, and stored until use. Paraffin-embedded sections were stained for the following:

Collagen: Collagen volume fraction was determined by analysis of picrosirius stained sections. Sections cut to 5 μm thickness were deparaffinized, stained with Weigert's hematoxylin, then stained with picrosirius red (0.1% Sirius Red in picric acid). Sections were subsequently washed and dehydrated before image analysis.

Cardiomyocyte cross sectional area: Heart sections were deparaffinized and permeabilized, then stained with wheat germ-agglutinin conjugated to Alexa488 (WGA-Alexa488, Invitrogen, W11261) at a concentration of 50 μg/mL to identify sarcolemmal membranes and measure cardiomyocyte cross sectional area (described below).

Image collection and analysis. Fluorescent and bright field images were collected on an epifluorescence-microscope (Axioscope, Zeiss). Fibrosis and cross-sectional cardiomyocyte area were quantified using ImageJ software (NIH). To quantify fibrosis, collagen fibers were highlighted, and the red-stained pixels were counted to determine the percentage of pixels in each field that represented collagen fibers. Perivascular tissue was excluded from this calculation. Three heart sections from each animal were imaged at five images per heart. Images were averaged for each animal and graphed in Prism GraphPad. Cardiomyocytes from WGA stained sections were randomly selected in a blinded fashion then traced to determine the cross sectional area of individual myocytes (n=100).

All images were captured and analyzed in a single-blind manner, except for WGA staining, which was analyzed in a double-blind manner.

RT-PCR. For RNA extraction, hearts were collected from mice and total RNA was isolated from homogenized hearts with Trizol (Molecular Research Center, TR 118) and further purified with an RNA isolation kit (Mo Bio Laboratories, Inc, 15000-250). Single-stranded cDNA was synthesized from 1 ug of total RNA using a cDNA synthesis kit (Qiagen, 205113). The mRNA levels of chymase (CMA1), atrial natriuretic peptide (ANP), TGF-, collagen III, matrix metalloproteinase (MMP) 2 and 9 and cyclophilin (CPN) were quantified by RT-PCR in triplicate with QuantiTect SYBR Green (Qiagen, 204245) in an Opticon device (MJ Research, Waltham, MA). The following primer pairs were used: ANP, 5'-AGA AAC CAG AGA GTG GGC AGA G-3' (SEQ ID NO. 1) and 5'-CAA GAC GAG GAA GAA GCC CAG-3' (SEQ ID NO. 2); TGFβ, 5'-TGG AGC AAC ATG TGG AAC TC-3' (SEQ ID NO. 3) and 5'-CAG CAG CCG GTT ACC AAG-3' (SEQ ID NO. 4); MMP2, 5'-TGG TGT GGC ACC ACC GAG GA-3' (SEQ ID NO. 5) and 5'-GCA TCG GGG GAG GGC CCA TA-3' (SEQ ID NO. 6); MMP9, 5'-CGG CAC GCC TTG GTG TAG CA-3' (SEQ ID NO. 7) and 5'-TCG CGT CCA CTC GGG TAG GG-3' (SEQ ID NO. 8); Collagen III, 5'-GAC CGA TGG ATT CCA GTT CG-3' (SEQ ID NO. 9) and 5'-TGT GAC TCG TGC AGC CAT CC-3' (SEQ ID NO. 10); CMA1, 5'-AGC TCA CTG TGC GGG AAG GTC T-3' (SEQ ID NO. 11) and 5'-CTC AGG GAC CAG GCA GGG CTT-3' (SEQ ID NO. 12).

Western blot analysis. Hearts were collected, and protein extracts were prepared from homogenized heart tissue using IGEPAL. Total protein concentrations were determined by the bicinchoninic acid (BCA) colorimetric assay. Absorbance was measured at 562 nm by spectrophotometer (Spectra Max 340), and concentrations determined using a standard curve based on bovine serum albumin (BSA) protein standards. Concentrations were normalized to 30 μg, and samples were separated by sodium dodecyl sulfate-polyacrylamide gel electrophoresis (SDS-PAGE). Protein samples were transferred to polyvinylidene fluoride (PVDF, Millipore, IPFL00010) membrane at 1.4 amps for 3.5 hours. Membranes were probed overnight at 4° C. with antibodies to cleaved Caspase-3 (Cell Signaling, 9661S), CMA1 (Gene Tex, GTX72388), and GAPDH (Calbiochem, CB100l). The membranes were visualized with ECL substrate (GE Healthcare, RPN2132) and film. Western blot band intensity was quantified as integrated density by densitometry and normalized to the density of loading control.

Any suitable TRPV1 inhibitor or combination of TRPV1 inhibitors may be used in the compositions and methods of the present invention. Inhibitors of TRPV1 family members, as used herein, are substances that reduce (partially, substantially, or completely block) the activity of one or more members of the TRPV1 family, that is, Trpv1, among others. The substances may be compounds (small molecules of less than about 10 kDa, peptides, nucleic acids, lipids, etc.), complexes of two or more compounds, and/or mixtures, among others. Furthermore, the substances may inhibit TRPV1 family members by any suitable mechanism including competitive, noncompetitive, uncompetitive, mixed inhibition, and/or by changing a subject's pH, among others. The expression "TRPV1 inhibitor" may refer to a product which, within the scope of sound pharmacological judgment, is potentially or actually pharmaceutically useful as an inhibitor of TRPV1, and includes reference to substances which comprise a pharmaceutically active species and are described, promoted, and/or authorized as a TRPV1 inhibitor. The strength of inhibition for a selective inhibitor may be described by an inhibitor concentration at which inhibition occurs (e.g., an $IC_{50}$ (inhibitor concentration that produces 50% of maximal inhibition) or a $K_i$ value (inhibition constant or dissociation constant)) relative to different TRPV1 family members.

Any suitable TRPV1 inhibitor or combination of inhibitors may be used in the methods and compositions herein. For example, a subject may be treated with a TRPV1 selective inhibitor and a nonselective TRPV1 inhibitor.

TRPV1 inhibitors include, but are not limited to:

| | |
|---|---|
| (N-(4-tertiarybutylphenyl)-4-(3-chloropyridin-2-yl) tetrahydropyrazine-1(2H)-carboxamide (BCTC) | Bio Trend (Switzerland) |
| N-(3-Methoxyphenyl)-4-chlorocinnamide (SB-366791) | *Neurosci.Lett.* 385: 137-142 |
| 1-lsoquinolin-5-yl-3-(4-trifluoromethyl-benzyl)-urea (A-425619) | *Eur. J. Pharmacol.* 596: 62-69 |
| (2E)-N-(2,3-Dihydro-1,4-benzodioxin-6-yl)-3-[4-(1,1-dimethylethyl)phenyl]-2-propenamide (AMG-9810) (AZD1386) | *J. Med. Chem.* 50: 3515-3527 Phase II-AstraZeneca |
| 2-Acetylamino-4-[6'-(4-trifluoromethylphenyl)-pyrimidin-4'-yl-oxy]-benzothiazole (AMG517) | |
| N-(2-bromophenyl)-N'-[((R)-1-(5-trifluoromethyl-2-pyridyl)pyrrolidin-3-yl)]urea (SB705498) | Phase II |
| N-(2-bromophenyl)-N'-{2-[ethyl(3-methylphenyl)amino]ethyl}-urea (SB-452533) | |
| ((R)-(5-tert-butyl-2,3-dihydro-1H-inden-1-yl)-3-(1H-indazol-4-yl)-urea (ABT-102) | |
| N-(Isoquinolin-5-yl)-N'-[spiro-(cyclobutane-1,2'-(3',4'-dihydro-benzopyran-4'-yl))]-urea (GRC-6211) | Phase II |
| (2R)-4-(3-chloro-2-pyridinyl)-2-methyl-N-[4-(trifluoromethyl)phenyl]-1-piperazinecarboxamide | |
| 4-(4'-Trifluoromethyl-anilino)-7-(3'-trifluoromethyl-pyridin-2-yl)-quinazoline (MK-2295) | Phase II |
| JYL 1421 | *Eur. J. Pharmacol.* 517: 35-44 |
| N-[2-(4-chlorophenyl)ethyl]-1,3,4,5-tetrahydro-7,8-dihydroxy-2H-2-benzazepine-2-carbothioamide (Capsazapine) | |
| (5R*,8R*,6E,9E)-5,8-Dimethyl-4-methylenetetradeca-6,9-dienoic acid | |
| 1-(3-Fluorobenzyl)-2-(N-(1,2-dimethyl-1,3-isoindazol-5-yl)-acetamido)-{pyridine-[3,4-b]-pyrrole} (SAR-115740) | |
| N-(4-chlorobenzyl)-N'-(1-methyl-1H-indazol-4-yl)urea, N-(4-tert-butylbenzyl)-N'-(1-methyl-1H-indazol-4-yl)urea, N-(3-fluoro-4-(trifluoromethyl)benzyl)-N'-(1-methyl-1H-indazol-4-yl)-urea, N-(4-fluoro-3-(trifluoromethyl)-benzyl)-N'-(1-methyl-1H-indazol-4-yl)-urea, N-(3,4-dichlorobenzyl)-N'-(1-methyl-1H-indazol-4-yl)urea, N-(2,4-dichlorobenzyl)-N'-(1-methyl-1H-indazol-4-yl)urea, N-(4-ethylbenzyl)-N'-(1-methyl-1H-indazol-4-yl)urea, N-(2-chlorobenzyl)-N'-(1-methyl-1H-indazol-4-yl)urea, N-(4-fluorobenzyl)-N'-(1-methyl-1H-indazol-4-yl)urea, N-(2-fluorobenzyl)-N'-(1-methyl-1H-indazol-4-yl)urea, N-[1-(bromophenyl)ethyl-N'-(1-methyl-1H-indazol-4-yl)urea, N-(1-methyl-1H-indazol-4-yl)-N'-{4-[(trifluoromethyl)thio]benzyl}urea. | Abbott Laboratories (20100249203) |

-continued 1-(2,3-dichlorophenyl)-3-[2-(N-ethyl-3-methylanilino)ethyl]urea
1-[2-(N-ethyl-3-methylanilino)ethyl]-3-naphthalen-1-ylurea
1-(4-bromophenyl)-3-[2-(N-ethyl-3-methylanilino)ethyl]urea
1-(3-bromophenyl)-3-[2-(N-ethyl-3-methylanilino)ethyl]urea
1-(chlorophenyl)-3-[2-(N-ethyl-3-methylanilino)ethyl] urea
1-[2-(N-ethyl-3-methylanilino)ethyl]-3-(2-fluorophenyl)urea
1-[2-{N-ethyl-3-methylanilino)ethyl]-3-(2-methylphenyl)urea
1-[2-(N-ethyl-3-methylanilino)ethyl]-3-phenylurea
2-[(2-bromophenyl)carbamoylamino]ethyl-ethylmethyl-(3-methylphenyl)azanium iodide
1-(2-bromophenyl)-3-[2-(N-ethyl-3-fluoro-4-methylanilino)ethyl] urea
1-(2-bromophenyl)-3-[2-(N-ethyl-3,4-difluoroanilino)ethyl] urea
1-(2-bromophenyl)-3-[2-(N-ethyl-3-fluoroanilino)ethyl] urea
1-(2-bromophenyl)-3-[2-(N-ethyl-4-methylanilino)ethyl]urea
1-(2-bromophenyl)-3-[2-(N-ethyl-2-methylanilino)ethyl]urea
1-(2-bromophenyl)-3-[2-(N-ethylanilino)ethyl]urea
N-[2-[(2-bromophenyl)carbamoylamino]ethyl]-N-(3-methylphenyl)acetamide
1-[2-{N-benzyl-3-methylanilino)ethyl]-3-(2-bromophenyl)urea
1-(2-bromophenyl)-3-[2-(2,3-dimethylanilino)ethyl] urea
1-(2-bromophenyl)-3-[2-(3-methylanilIino)ethyl]urea
1-(2,5-dichlorophenyl)-3-[2-(N-ethyl-3-methylanilino)ethyl] urea
2,6-bis-(4-hydroxy-3-methoxybenzylidene) cyclohexanone(BHMC)
4-fluoro-4-(3-methylpyridin-2-yl)-N-[4-trifluoromethylphenyl]piperidine-1-carboxamide
4-fluoro-4(pyridin-2-yl)N-[4-trifluoromethylphenyl] piperidine-1-carboxamide
4-fluoro-4(pyridine-2-yl)N-[4-trifluoromethylbenzyl] piperidine-1-carboxamide
2-{4-fluoro-1-[4-trifluoromethylbenzoyl]piperidin-4-yl}pyridine
2-(4-fluoro-1-{[4-trifluoromethylphenyl]acetyl} piperidin-4-yl)pyridine
2-(4-fluoro-1-{3-[4-trifluoromethylphenyl]propanoyl} piperidin-4-yl)pyridine
4-fluoro-4-(1-methyl-1H-imidazol-2-yl)-N-[4-trifluoromethylphenyl]piperidine-1-carboxamide
4-methoxy-4-pyridin-2-yl-N-[4-trifluoromethylphenyl]piperidine-1-carboxamide
4-methoxy-4-pyridin-2-yl-N-[4-trifluoromethylbenzyl]piperidine-1-carboxamide
4-fluoro-N-(4-isopropylphenyl)-4-(3-methylpyridin-2-yl)piperidine-1-carboxamide
4-fluoro-4-(3-methylpyridin-2-yl)-N-{4-[1,2,2,2-tetrafluoro-1-trifluoromethyl-ethyl]phenyl}piperidine-1-carboxamide
N-(4-Tert-butylphenyl)-4-fluoro-4-(3-methylpyridin-2-yl)piperidine-1-carboxamide
4-fluoro-4-(3-methylpyridin-2-yl)-N-[4-(pentafluoro-lambda(sup 6)-sulfanyl)phenyl]piperidine-1-carboxamide
N-(4-Butylphenyl)-4-fluoro-4-(3-methylpyridin-2-yl) piperidine-1-carboxamide
N-(4-Benzylphenyl)-4-fluoro-4-(3-methylpyridin-2-yl)piperidine-1-carboxamide
N-biphenyl-4-yl-4-fluoro-4-(3-methylpyridin-2-yl) piperidine-1-carboxamide
4-fluoro-4-(3-methylpyridin-2-yl)-N-[5-trifluoromethylpyridin-2-yl]piperidine-1-carboxamide
4-(3-chloropyridin-2-yl)-4-fluoro-N-[4-trifluoromethylphenyl]piperidine-1-carboxamide
4-fluoro-4-(3-fluoropyridin-2-yl)-N-[4-trifluoromethylphenyl]piperidine-1-carboxamide
4-fluoro-4-(3-methoxypyridin-2-yl)-N-[4-

-continued trifluoromethylphenyl]piperidine-1-carboxamide 4-
fluoro-4-(3-methylpyridin-2-yl)-N-[4-
trifluoromethylphenyl]piperidine-1-carbothioamide
N'-cyano-4-fluoro-4-(3-methylpyridin-2-yl)-N-
[4-trifluoromethylphenyl]piperidine-1-carboximidamide
4-fluoro-4-(3-methylpyridin-2-yl)-N'-(1-
phenylpiperidin-4-yl)-N-[4-trifluoro-methylphenyl]
piperidine-1-carboximidamide
4-fluoro-4-phenyl-N-[4-trifluoromethylphenyl]
piperidine-1-carboxamide
(+/−)-(syn)-4-fluoro-2-methyl-4-(3-methylpyridin-2-yl)-
N-[4-trifluoromethyl-phenyl]piperidine-1-carboxamide
4-(fluoromethyl)-4-pyridin-2-yl-N-[4-
trifluoromethylphenyl]piperidine-1-carboxamide
syn- and anti-3-fluoro-3-pyridin-2-yl-N-[4-
trifluoromethylphenyl]-8-azabicyclo[3.2-.1]octane-8-
carboxamide
3-fluoro-3-pyridin-2-yl-N-[4-trifluoromethylphenyl]-8-
azabicyclo[3.2.1]octane-8-carboxamide
4-fluoro-4-pyrimidin-2-yl-N-[4-
trifluoromethylphenyl]piperidine-1-carboxamide
4-fluoro-4-(3-phenylpropyl)-N-[4-
trifluoromethylphenyl]piperidine-1-carboxamide
2-[4-fluoro-4-(3-methylpyridin-2-yl)piperidin-1-yl]-6-
trifluoromethyl-1H-benzimidazole
2-(4-fluoro-4-pyridin-2-ylpiperidin-1-yl)-6-
(trifluoromethyl)-1H-benzimidazole
4-fluoro-N-[4-trifluoromethylphenyl]-4-[3-
trifluoromethylpyridin-2-yl]piperidine-1-carboxamide
4-fluoro-N-(4-methylphenyl)-4-(3-methylpyridin-2-
yl)piperidine-1-carboxamide
N-(4-ethylphenyl)-4-fluoro-4-(3-methylpyridin-2-yl)
piperidine-1-carboxamide
N-(4-chlorophenyl)-4-fluoro-4-(3-methylpyridin-2-
yl)piperidine-1-carboxamide
4-fluoro-4-(3-methylpyridin-2-yl)-N-[4-
trifluoromethoxyphenyl]piperidine-1-carboxamide N-(4-
cyanophenyl)-4-fluoro-4-(3-methylpyridin-2-yl)
piperidine-1-carboxamide
N-[4-dimethylaminophenyl]-4-fluoro-4-(3-
methylpyridin-2-yl)piperidine-1-carboxamide
1-(2-(3,3-dimethylbutyl)-4-(trifluoromethyl)benzyl)-
3-(1-methyl-1H-indazol-4-yl)urea
N-acetyl-1-phenylalanyl-1-leucinamide
Nobilamides A-H
(Lin 2011)
SB366791
(Gunthrope 2004)
TRPV1 antagonists
(Messeguer 2006)
Capsaicin receptor ligands
PCT WO 02/08221

Pharmaceutically acceptable salts forming part of this invention include base addition salts such as alkali metal salts like $Li^+$, $Na^+$, and $K^+$ salts, alkaline earth metal salts like $Ca^{2+}$ and $Mg^{2+}$ salts, salts of organic bases such as lysine, arginine, guanidine, diethanolamine, choline and the like, ammonium or substituted ammonium salts. Salts may include acid addition salts which are sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. The term pharmaceutically acceptable solvates includes combinations of solvent molecules with molecules or ions of the solute compound (the inhibitor). Pharmaceutically acceptable solvates may be hydrates or comprising other solvents of crystallization such as alcohols.

Preferred salts for the list of compounds above are hydrochloride, hydrobromide, sodium, potassium or magnesium.

The present invention provides pharmaceutical compositions containing a TRPV1 inhibitor or mixture of TRPV1 inhibitors. An inhibitor may be in the form if a pharmaceutically acceptable salt or a pharmaceutically acceptable solvate in combination with the usual pharmaceutically employed carriers, diluents and the like.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. Pharmaceutically acceptable solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The pharmaceutical compositions of the invention are shown to be effective by tests in animal models. The pharmaceutical compositions of the invention are thus effective for treatment of cardiac hypertrophy in a mammalian subject, including cardiac remodeling, cardiac fibrosis, apoptosis, hypertension, or heart failure. The compositions may also be administered for prophylactic treatment of cardiac hypertrophy in a mammalian subject.

Generally, the effective dose for treating a particular condition in a patient may be readily determined and adjusted by the physician during treatment to alleviate the symptoms or indications of the condition or disease. Generally, a daily dose of active compound (inhibitor) in the range of about 0.01 to 1000 mg/kg of body weight is appropriate for administration to obtain effective results. The daily dose may be administered in a single dose or divided into several doses. In some cases, depending upon the individual response, it may be necessary to deviate upwards or downwards from the initially prescribed daily dose. Typical pharmaceutical preparations normally contain from about 0.2 to about 500 mg of active compound of formula I and/or its pharmaceutically active salts or solvates per dose.

The term "therapeutically effective amount," "pharmaceutically effective amount," or "effective amount" refers to that amount of a compound or mixture of compounds of Formula I that is sufficient to effect treatment, as defined below, when administered alone or in combination with other therapies to a mammal in need of such treatment. The term "mammal" as used herein is meant to include all mammals, and in particular humans. Such mammals are also referred to herein as subjects or patients in need of treatment. The therapeutically effective amount will vary depending upon the subject and disease condition being treated, the weight and age of the subject, the severity of the disease condition, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease or condition, that is, causing the clinical symptoms of the disease not to develop;

b) inhibiting the disease, that is, slowing or arresting the development of clinical symptoms; and/or c) relieving the disease, that is, causing the regression of clinical symptoms.

The invention is explained in detail in the examples given below which are provided by way of illustration only and therefore should not be construed to limit the scope of the invention.

Example 1

Trpv1 Knockout Suppresses Pressure Overload Cardiac Hypertrophy

Pressure overload cardiac hypertrophy was modeled by transverse aortic constriction (TAC) in 8 week old male TRPV1 knockout mice (Caterina, 2000) and wild type controls. Sham control mice underwent the same procedure except for aortic constriction. Baseline pressures were assessed proximal; and distal, to the TAC banding site, as analyzed by Doppler echo. There was no significant difference between Trpv1$^{-/-}$ and control animals. Transthoracic echocardiography (Echo) was performed using a high resolution Vevo 770™ Echo system with a 30 MHz transducer (Visual Sonics, Toronto, Canada) in unanesthetized mice, in order to assess heart dimensions during pressure overload cardiac hypertrophy, as compared to sham controls. Mice were sacrificed at 6 weeks post TAC, and hearts were collected for histological sectioning, RNA extraction, and protein analysis by Western blot and other methods. Gravimetric analyses of cardiac hypertrophy at 6 weeks after TAC, indicate that the heart weight/body weight ratio, as well as the heart weight/tibia length ratio increases more in the control animals than the Trpv1$^{-/-}$ hearts, as compared to sham animals. Referring to FIG. 1A the effects of TAC are shown in banded animals on left ventricle (LV) internal diameter, diastolic, from baseline to 6 weeks in C57BU6 WT (n=17), Trpv1$^{-/-}$ (n=15), compared to those effects (FIG. 1B) in sham operated animals (n=9) (middle). In FIG. 1C the effects of TAC are shown on rate of LVID change/day in C57BU6 WT (n=17) versus Trpv1$^{-/-}$ (n=15). (P<0.05) WT and Trpv1$^{-/-}$ (p<0.05). In FIG. 1D the effects of TAC on treated animals on LV function (fractional shortening) from baseline to 8 weeks in C57BU6

WT (n=17), Trpv1$^{-/-}$ (n=15), and on sham operated animals C57BU6 WT (n=9), Trpv1$^{-/-}$ (n=9). Most notably, in FIG. 1C there is shown a significant increase in the rate of left ventricle internal diameter, in control mice (n=17) as compared to Trpv$^{-/-}$ mice (n=15) (P<O.OS). Sham Trpv$^{-/-}$ and control animals did not differ significantly. FIG. 1D indicates that left ventricular function as measured by percentage fractional shortening (% FS=([LVDd−LVDs]/[LVDd]×100) appears to be preserved in Trpv1$^{-/-}$ mice from zero to four weeks, as compared to control animals, but declines from four to six weeks.

Example 2

Figure 2:
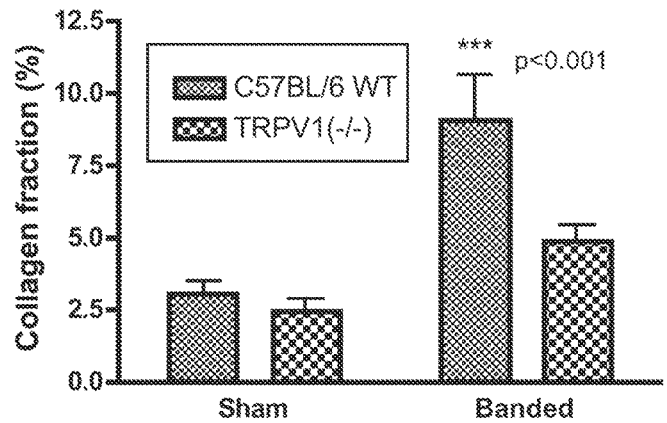
FIG. 2 is a graph of results of data obtained by the picrosirius staining procedure described in Example 2.
Figure 3A:
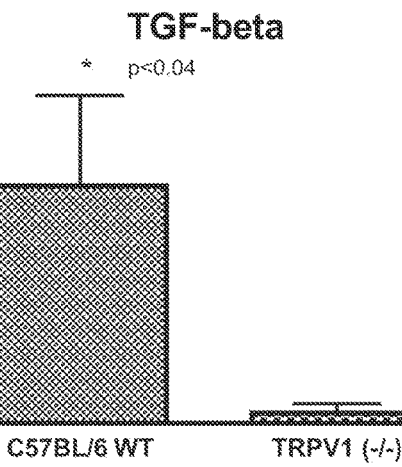
FIGS. 3A-3B are graph of results of data obtained by the TGF-beta RNA expression and ANP expression procedures described in Example 2.
Figure 3B:
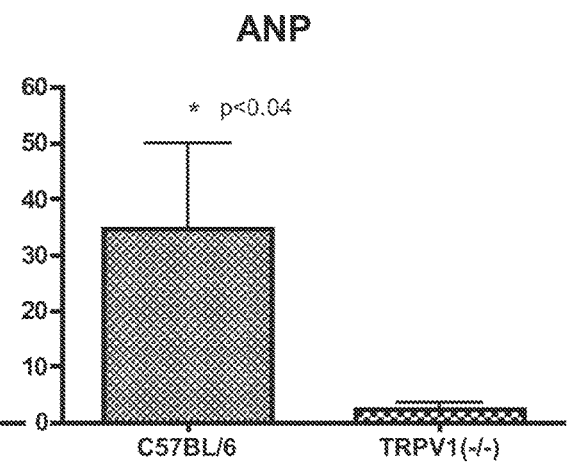

Trpv1 Knockout Alters Hypertrophic Markers in Pressure Overload Cardiac Hypertrophy Multiple hypertrophy markers were analyzed from extracted heart lysates and sections. Overall, major hypertrophic indicators like collagen (FIG. 2), atrial natriuretic peptide and TGFβ (FIGS. 3A, 3B) show a significant reduction in expression in Trpv1$^{-/-}$ mice modeled with pressure overload cardiac hypertrophy for six weeks. In FIG. 2 quantification of picrosirius staining in TRPV1 deficient and C57BU6 WT controls are shown, performed in Image J, excluding perivascular tissue. Each heart was stained in replicates of 3. Image J was used to analyze 5 images from each heart (×3) and determine the pixel count in each field as percentage of overall number of pixels for a ratio of red-stained collagen/fiber:total tissue area. Images were averaged for each animal and graphed in Prism GraphPad; p<0.001 between TRPV1 banded and C57BU6 banded. In FIG. 3A are shown TGF-beta RNA expression in C5781/6 (n=7), and TRPV1−/− (n=4) (p<0.0328). In FIG. 3B are shown ANP expression in C5781/6 (n=15), and TRPV1 (n=14) (p<0.0431). Total RNA was isolated from homogenized hearts with Trizol (Molecular Research Center) and further purified with a RNA isolation kit (Mo Bio Laboratories, Inc). Single-stranded cDNA was synthesized from 1 μg of total RNA using a cDNA synthesis kit (Qiagen). The mRNA levels were quantified by RT-PCR using SYBR green method.

Example 3

Extracellular Matrix Remodeling

The composition of cardiac tissue changes during the development of ventricular hypertrophy and leads to structural remodeling of the myocardium. One of these changes is related to the disruption of the equilibrium between the synthesis and degradation of collagen, which results in an excessive accumulation of collagen type I and III fibers within the myocardium. As collagen and other extracellular matrix components accumulate in the interstitial space, myocardial stiffness increases and diastolic and systolic dysfunction occurs. Prior data indicates less interstitial collagen deposition in the Trpvr1$^{-/-}$ mice than control mice, with pressure overload cardiac hypertrophy (Buckley 2011). Similar results were obtained by collagen protein assay (Sircol™, Biocolor, Northern Island), and RealTime-PCR. Changes are also seen in the enzymes responsible for degradation of collagen, the matrix metalloproteinases (MMPs). (FIGS. 4A, 4B)

Figure 4A:
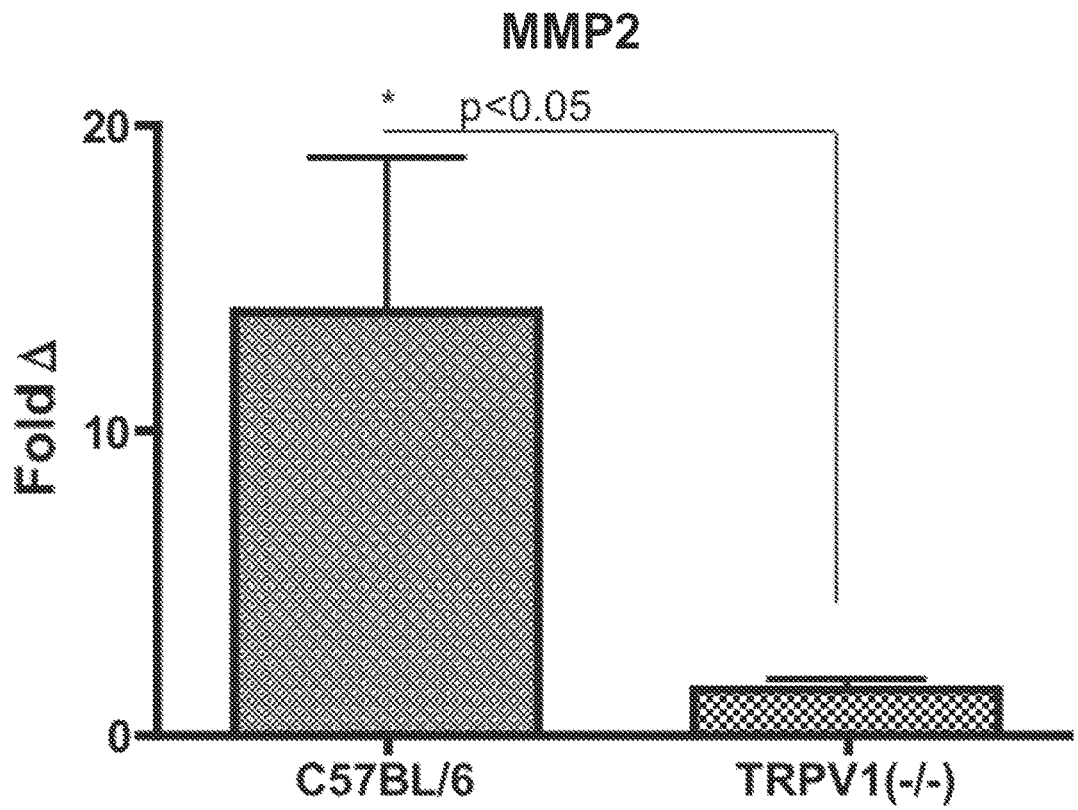
FIGS. 4A-4B are graphs of results of data obtained by the procedures described in Example 3.
Figure 4B:
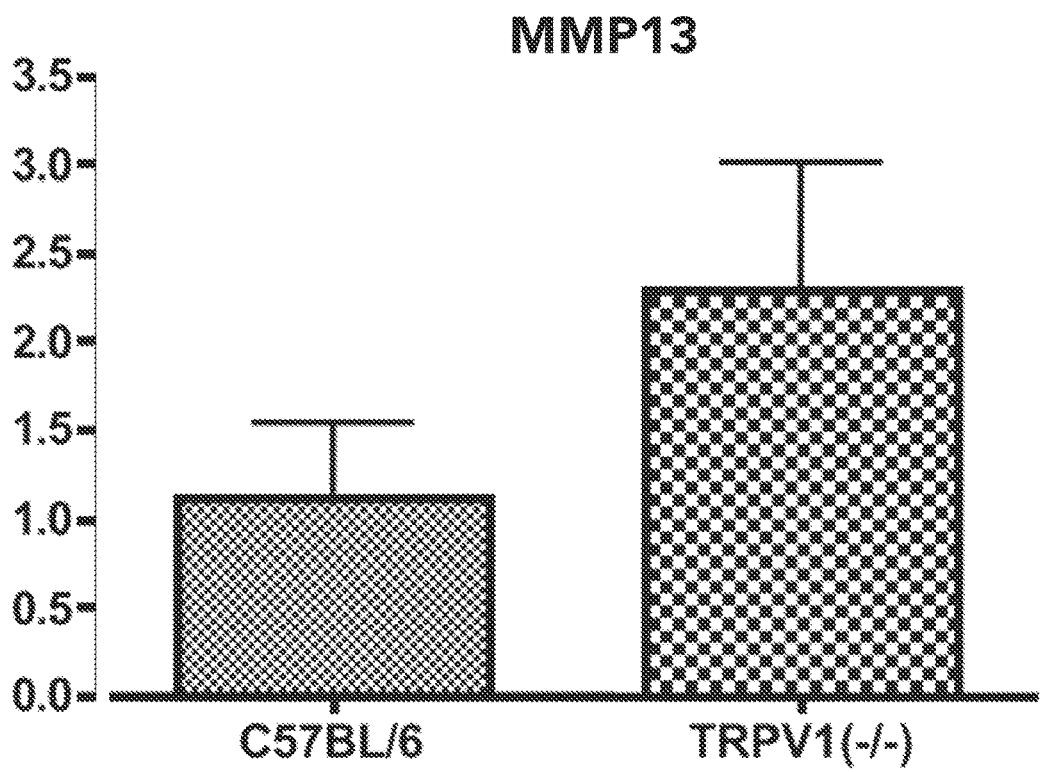
Figure 7A:
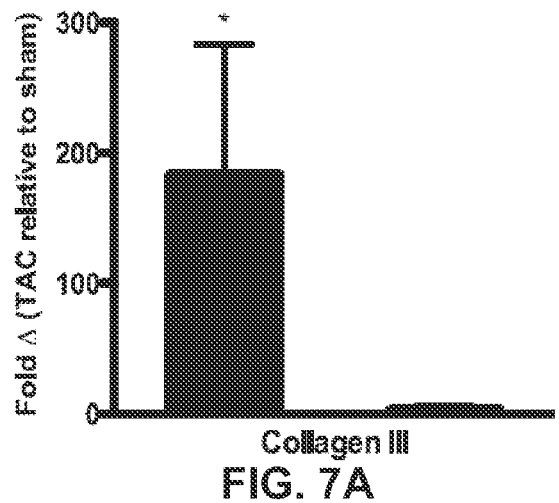
FIGS. 7A-7E are graphs of test results on measurement of fibrosis, tissue remodeling, and inflammatory markers by procedures described in Example 4.
Figure 7B:
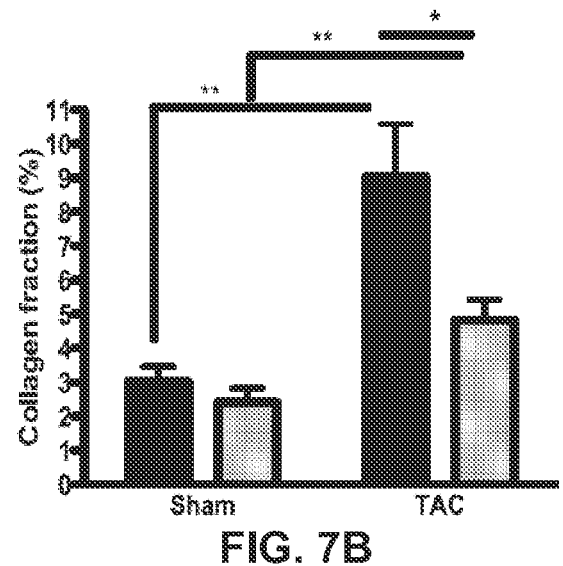
Figure 7C:
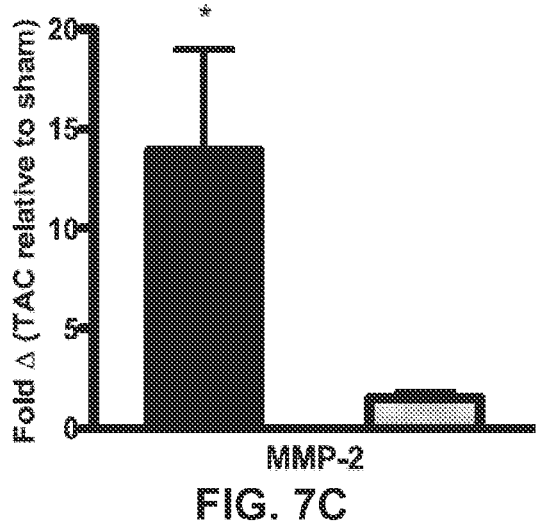
Figure 7D:
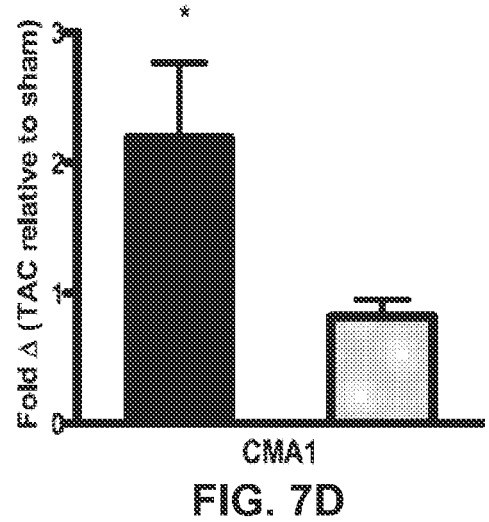

The RNA expression changes in sham vs. TAC treated mice shown in FIG. 4A for MMP2 by RT-PCR (p<0.05). C5781/6 (n=15), and Trpv1$^{-/-}$ (n=14), and in FIG. 4B for MMP13 by RT-PCR. Generally, suppression of Mmp and Timp transcription is observed more in the Trpv1$^{-/-}$ mice than in control mice 6 weeks post TAC. However, MMP13 appears upregulated. MMP13 targets collagen type I, II and III and may serve to protect tissue from fibrosis. Mast cell chymase (CMA 1) message and protein is expressed less in Trpv1$^{-/-}$ mice than in control mice 8 weeks post TAC (FIG. 7D). CMA1 is a chymotryptic serine proteinase that belongs to the peptidase family S1. It is described as expressed in mast cells but appears to be expressed in other tissues and cell types. It functions in the degradation of the extracellular matrix and the generation of vasoactive peptides. In the heart and blood vessels, this protein, rather than angiotensin converting enzyme (ACE), is largely responsible for converting angiotensin I to the vasoactive peptide angiotensin II in the renin-angiotensin system. This system controls blood pressure and is involved in the pathogenesis of hypertension, cardiac hypertrophy, and heart failure.

Example 4

Involvement of TRPV1 in the Progression of Cardiac Hypertrophy

Mice lacking functional TRPV1 and control mice with wild-type TRPV1 were modeled for pressure overload cardiac hypertrophy. Heart dimensions and function were measured and compared over time using unanesthestized transthoracic echocardiography and hearts were harvested eight weeks later for molecular, biochemical and histological analysis. Heart dimensions and function were better preserved in mice lacking functional TRPV1. Cellular hypertrophy, markers for hypertrophy, fibrosis and apoptosis were also significantly reduced in these mice, indicating involvement of TRPV1 in the progression of cardiac hypertrophy.

Pressure Overload Model

To test the involvement of TRPV1 in the remodeling associated with cardiac hypertrophy and heart failure, ten-week-old male B6.129X1-Trpv1tm1Jul/J mice (TRPV1 KO), (Caterina, 2000) and age/sex matched C57BL/6J (WT) control mice were subjected to acute pressure overload by transverse aortic constriction (TAC). Sham operated control mice from both strains underwent an identical surgical procedure except for actual aortic constriction. TRPV1 KO TAC mice and WT TAC mice showed no difference in baseline pressures, assessed immediately distal to the TAC banding site by Doppler echocardiography.

Gravimetric Analysis of the Heart, after Pressure Overload Cardiac Hypertrophy

Figure 5A:
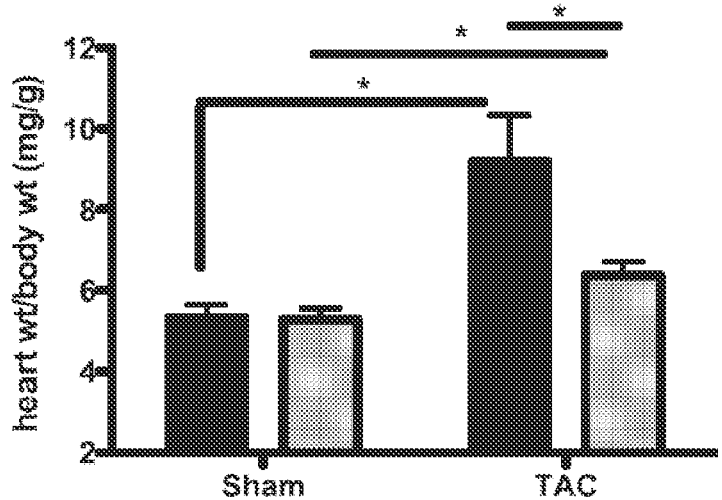
FIGS. 5A-5F are graphs of test results obtained by procedures described in Example 4 pertaining to gravimetric, structural, and functional analysis of the heart during and after applied pressure overload cardiac hypertrophy.
Figure 5B:
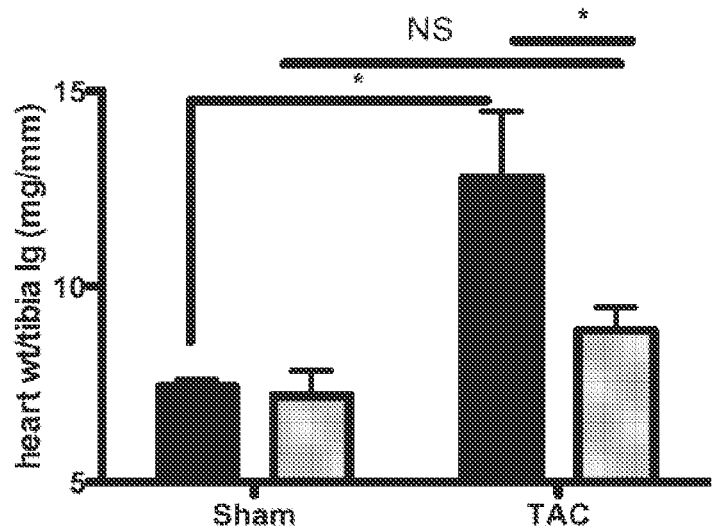

This analysis reveals that TAC treated hearts were 28% heavier in WT TAC mice than TRPV1 KO TAC mice. When normalized to body weight and tibia length, the heart weight/body weight ratio and the heart weight/tibia length ratio were also significantly greater in WT TAC mice than TRPV1 KO TAC mice. (FIGS. 5A and 5B) Mice lacking functional TR PV1 present preservation of heart structure and function during pressure overload cardiac hypertrophy. (■ WT ▨ TR PV1 KO). FIG. 5A is a graph showing heart weight/body weight (HW/BW) and heart weight/tibia length (HW/TL). There is significant difference in HW/BW between WT Sham and TAC mice (p=0.027), WT TAC and TR PV1 KO TAC mice (p=0.019) and TR PV1 KO Sham and TAC mice (p=0.045). FIG. 5B shows that there is significant difference in HW/TL between WT Sham and TAC mice (p=0.034), WT TAC and TR PV1 KO TAC mice (p=0.03), but not between TR PV1 KO Sham and TR PV1 KO TAC mice (p=0.095).

Heart Structure and Function are Maintained During Pressure Overload Cardiac Hypertrophy in Mice Lacking Functional TRPV1

Figure 5C:
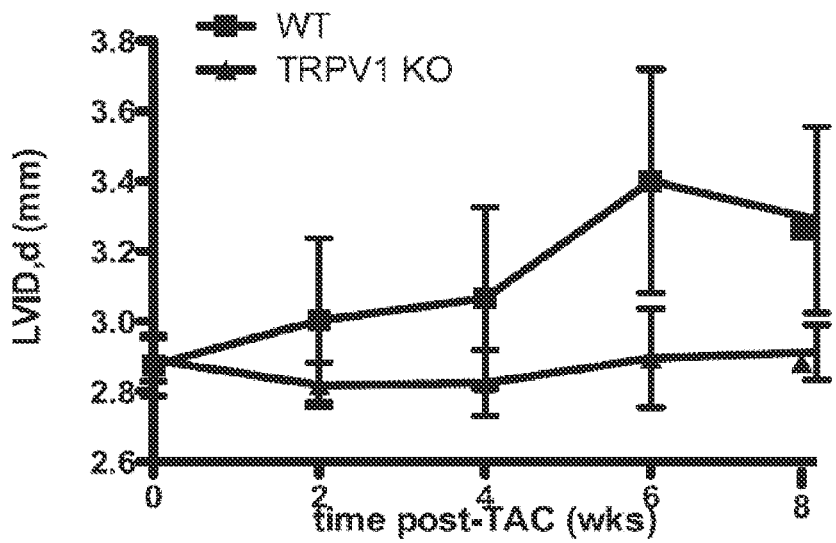
Figure 5D:
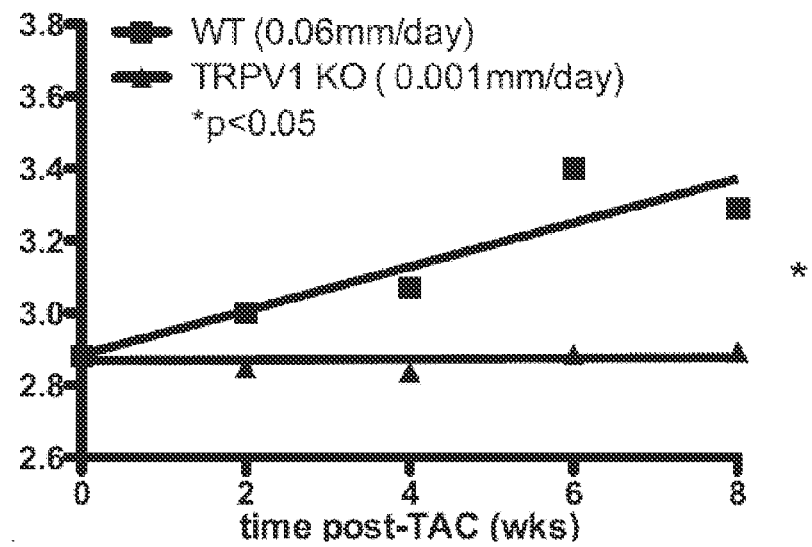
Figure 5E:
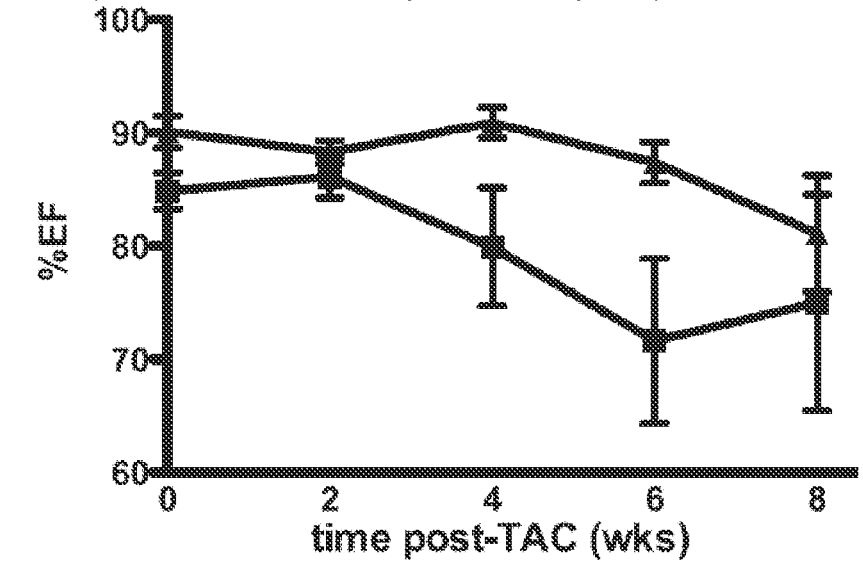
Figure 5F:
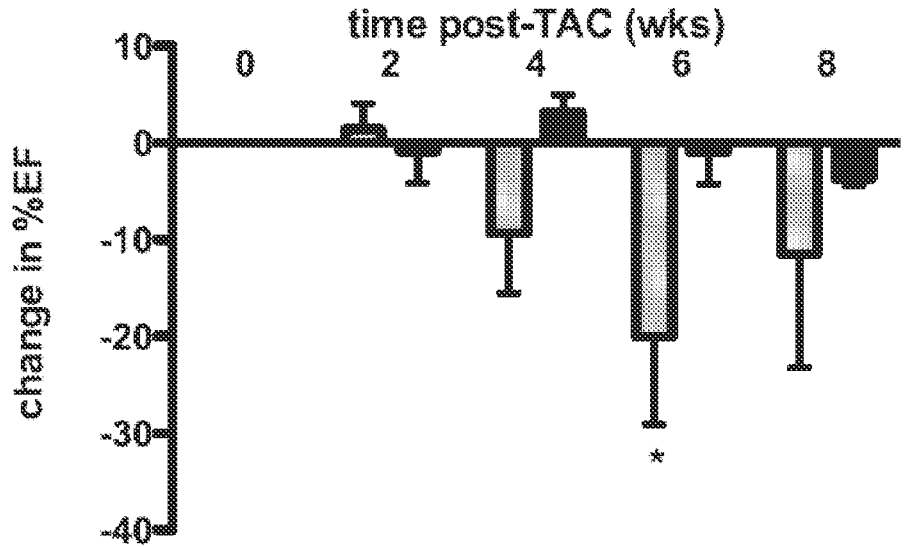

End-diastolic left ventricular internal diameter (LVIDd) was analyzed for eight weeks following TAC by transthoracic echocardiographic analysis. In WT TAC mice, LVIDd began to increase at two weeks and plateaued at approximately six weeks. The TRPV1 KO TAC mice showed no change in LVIDd until six weeks. FIG. 5C shows the analysis of left ventricular internal diameter end-diastolic (LVIDd) from zero to eight weeks in WT (n=6) and TR PV1 KO mice (n=8). The TAC WT control mice start increasing their internal diameter at two weeks, whereas in TAC TR PV1 KO mice there is a delay until six weeks post TAC treatment. The rate of increase in LVIDd is significantly greater in WT TAC mice than in TRPV1 KO TAC mice (FIG. 5D) between weeks two and six post TAC. FIG. 5D shows the rate of change in LVIDd from zero to eight weeks was significant (p=0.013) between TAC WT and TAC TR PV1 KO. Heart function was analyzed by left ventricular ejection fraction (% EF). Heart function declined in WT mice from approximately two to six weeks post TAC treatment, but was preserved in TRPV1 KO TAC mice over the same period of time. FIG. 5E shows a reduction in function starting at two weeks in TAC WT mice, but TAC TR PV1 KO mice are protected until six weeks, the percent change in ejection fraction was significantly different at six weeks (p=0.039). The change in ejection fraction at six weeks is significantly different between WT TAC mice and TRPV1 KO TAC mice (FIG. 5F).

Figure 6A:
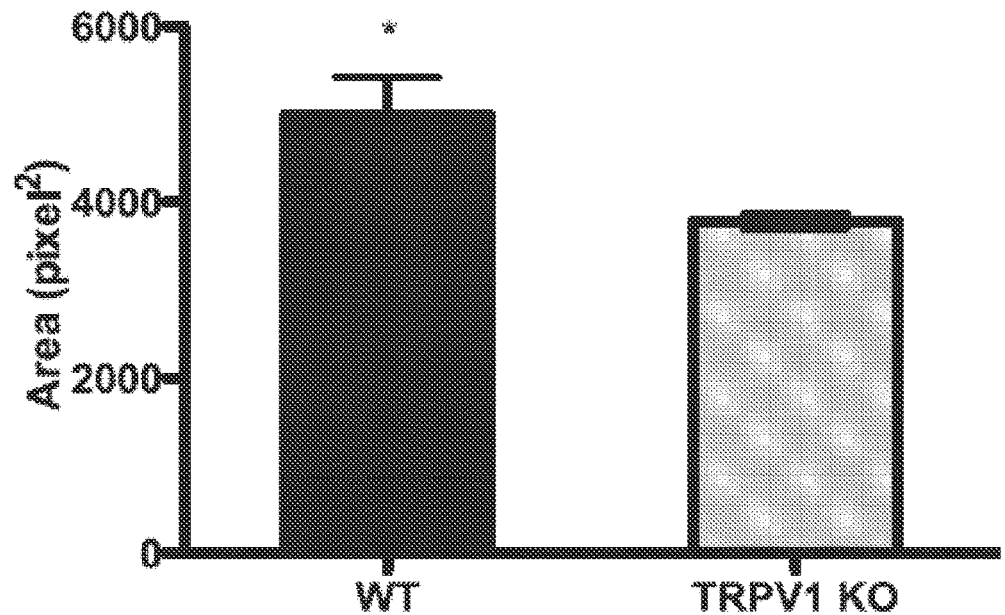
FIGS. 6A-6D are graphs of test results on measurement of cardiomyocyte cross sectional area, and expression levels of ANP and TGFβ by procedures described in Example 4.
Figure 6B:
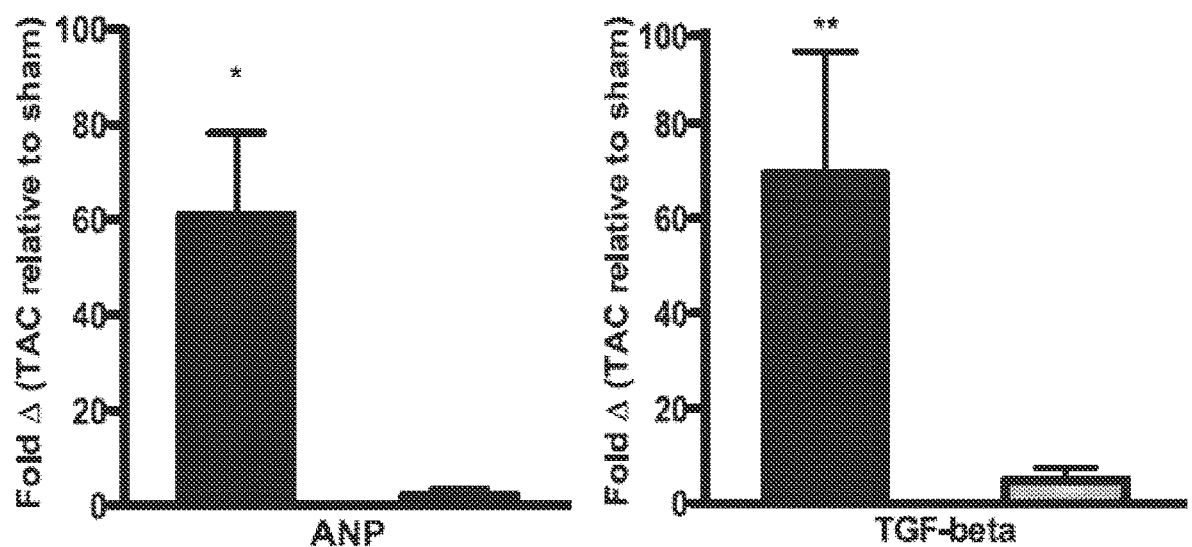
Figure 6C:
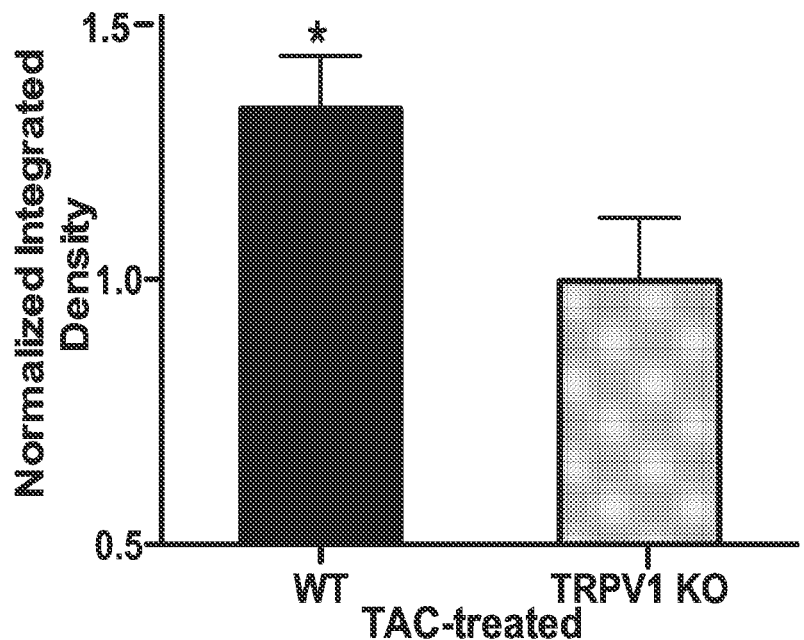
Figure 6D:
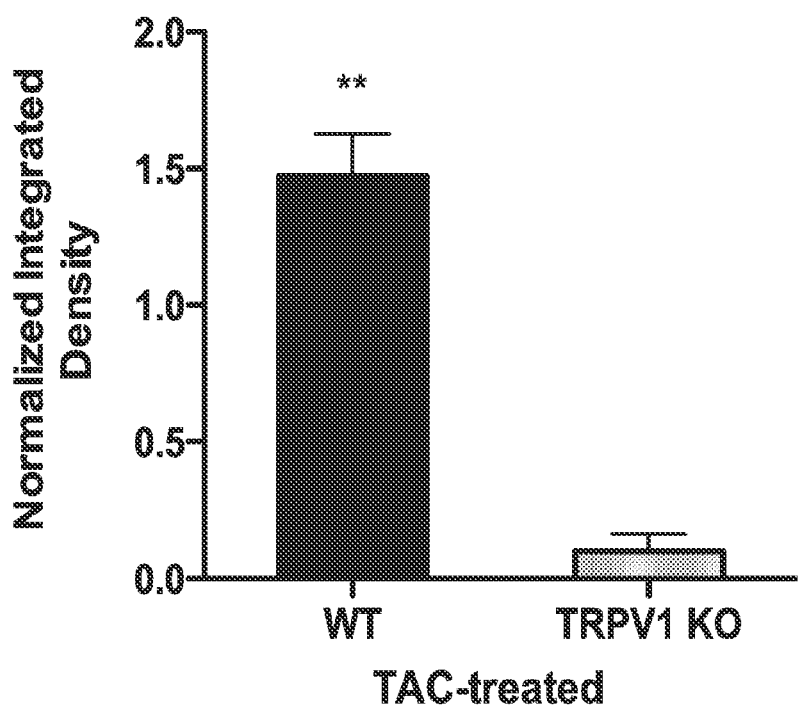

Mice Lacking Functional TRPV1 are Protected from Hypertrophy and Apoptosis after Modeled Pressure Overload Cardiac Hypertrophy The degree of cellular hypertrophy was examined by staining of the plasma membranes with fluorescently-labeled wheat germ agglutinin (WGA). Cell sizes were compared by imaging and computer aided measurement of the cross-sectional area of cardiomyocytes. This comparison reflects the degree of cellular hypertrophy between samples. (Shiojima, 2005) The data show a significant increase in the cardiomyocyte cross sectional area of WT TAC compared to TRPV1 KO TAC mice (FIG. 6A). Measurement of cardiomyocyte cross sectional area, was significantly different between TAC WT mice and TAC TR PV1 KO mice (p=0.025, n=100), 8 weeks post TAC treatment. This shows that, at the cellular level, TRPV1 KO mice develop less cardiac hypertrophy than WT mice, in response to modeled pressure overload cardiac hypertrophy. To further compare the degree of hypertrophy between TRPV1 and WT mice, additional markers of hypertrophy, apoptosis and heart failure were assessed. Plasma concentrations of the circulating hormone atrial natriuretic peptide (ANP) and the growth factor TGFbeta increase during heart failure and are considered late markers of cardiac hypertrophy. Therefore, expression of ANP and TGFbeta was analyzed by RT-PCR of mRNA isolated from heart tissue. Significantly greater increases were shown in ANP and TGFbeta transcript levels in WT TAC mice than in TRPV1 KO TAC mice. FIG. 6B shows that expression levels of atrial natriuretic peptide (ANP) and TGFbeta transcripts were significantly greater in TAC WT mice than in TRPV1 KO mice (p=0.037, p=0.007) relative to control mice. Western blot analysis confirmed that there was a significant increase (FIG. 6C) in ANP protein expression in TAC WT mice compared to TAC TRPV1 KO mice. These data show that protection from the stress and or signaling systems associated with the hypertrophic transcriptional responses is observed in the TRPV1 KO mice. The degree of cellular apoptosis by measurement of cleaved caspase-3 protein in heart tissue lysates from TAC and sham treated WT and TRPV1 KO mice were assessed. Analysis of western blot densitometry of heart tissue lysates showed significantly less caspase-3 cleavage in TRPV1 KO TAC mice than in WT TAC mice. As expected, WT sham and TRPV KO sham mice showed no apparent caspase-3 cleavage. (FIG. 6D) These results show that TAC-induced cardiac apoptosis is reduced in TRPV1 KO mice. There is protection from the stress and or signaling associated with cardiac hypertrophy in the TRPV1 KO mice.

Figure 7E:
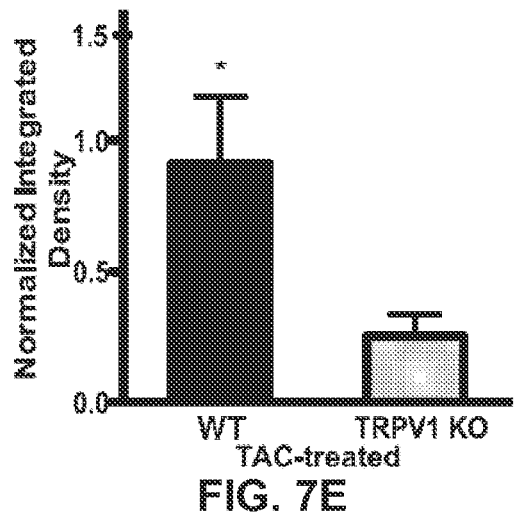

Mice Lacking Functional TRPV1 Show Reduced Fibrosis, Tissue Remodeling and Inflammatory Markers after Modeled Pressure Overload Cardiac Hypertrophy During the development of ventricular hypertrophy, the composition of cardiac tissue changes, leading to structural remodeling of the myocardium. For example, the disruption of the equilibrium between the synthesis and degradation of collagen results in an excessive accumulation of collagen type I and III fibers within the myocardium. As collagen and other extracellular matrix components accumulate in the interstitial space, myocardial stiffness increases, and diastolic and systolic dysfunction occurs. Collagen III levels were analyzed by RT-PCR and total collagen by histological staining, in heart tissue from Sham and TAC, WT and TRPV1 KO mice. It was shown that collagen III transcript levels (FIG. 7A), and interstitial collagen deposition (FIG. 7B) were reduced in hearts isolated from TRPV1 KO TAC mice compared to WT TAC mice. Mice lacking functional TR PV1 present with less interstitial fibrosis and tissue remodeling enzymes than WT control mice, eight weeks post TAC treatment. (■ WT ※ TR PV1 KO). FIG. 7A shows an increase in the expression of Collagen III transcript was significantly greater in TAC WT mice than in TAC TRPV1 KO mice (p=0.037, 0.007). In FIG. 7B mice lacking functional TR PV1 present with less interstitial fibrosis and tissue remodeling enzymes than WT control mice, eight weeks post TAC treatment. (■ WT ※ TR PV1 KO). There was a significant increase in MMP2 transcripts in hearts from WT TAC compared to hearts from TRPV1 TAC mice. FIG. 7C shows that increases in the expression matrix metalloproteinase-2 (MM P-2) transcript was significantly less in TAC treated TR PV1 KO mice than TAC treated WT mice (p=0.049). There was also significantly less expression of Chymase (CMA1) transcript (p=0.049). Mast cell chymase. CMA1, is a chymotryptic serine proteinase that belongs to the peptidase family S1. It functions in the degradation of the extracellular matrix and in the generation of vasoactive peptides. In the heart and blood vessels, it is CMA1, rather than angiotensin converting enzyme (ACE), that is largely responsible for converting angiotensin I to the vasoactive peptide angiotensin II. The data in FIGS. 7D and 7E show that CMA1 transcripts and protein are expressed at significantly higher levels in hearts from WT TAC mice than TRPV1 KO TAC mice. There was significantly less expression of Chymase (CMA1) transcript (p=0.049), and Chymasc protein (p=0.0218) in isolated heart tissue from TAC TR PV1 KO mice than TAC WT mice (CMA1 integrated density was normalized to GAPDH loading control). The data show that the functional knockout of TRPV1 in mice allows for the preservation of heart structure and heart function under modeled pressure overload. Concomitant with this protection is the down-regulation of multiple protein and transcriptional markers associated with initiation and the progression of hypertrophy, apoptosis, fibrosis, and heart failure. This data show that TRPV1 has a role as either an initiating stressor, or an upstream signaling transducer of the hypertrophic transcriptional response in the heart.

Example 5

Mice Treated with the TRPV1 Antagonist BCTC Present Preservation of Heart Mass, Structure and Function During Pressure Overload Cardiac Hypertrophy The following tests show that treatment by continuous administration using osmotic pumps with the TRPV1 antagonist, BCTC, in WT mice exposed to TAC confirms the findings from tests of the prior Examples.

Osmotic pump installation. Long term (up to 42 day) infusion of drugs can be accomplished by insertion of osmotic pumps without the need for repeated injection. Mice are placed under a low plane of anesthesia with an injection of Ketamine/Xylazine anesthetic (50 mg/10 mg·Kg) intraperitoneally (IP) 10 minutes prior to surgery. A small area between shoulder blades is shaved and sterilized with Povidine swab. A small incision is made in this area and blunt dissected below skin to allow placement of an Alzet osmotic pump (model 2006), previously loaded with the drug of choice under the skin between the shoulder blades where it is inaccessible to the mouse. Several stitches are applied to close the incision. The mouse is placed in regular housing on a warming mat until completely conscious, after which mice are then returned to regular housing room.

Figure 8A:
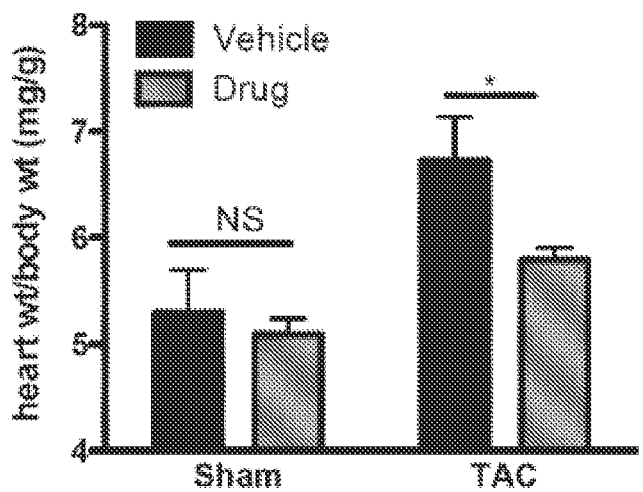
FIGS. 8A-8E are graphs of test results on measurement of heart mass, structure and function during pressure overload cardiac hypertrophy by procedures described in Example 5.
Figure 8B:
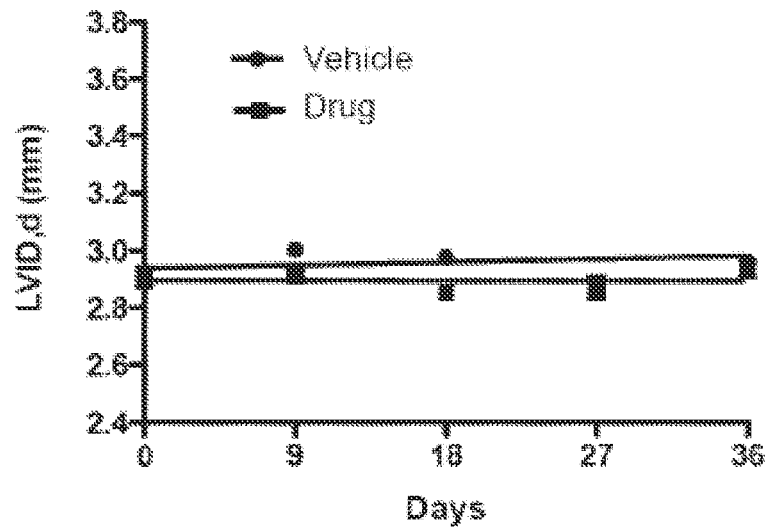
Figure 8C:
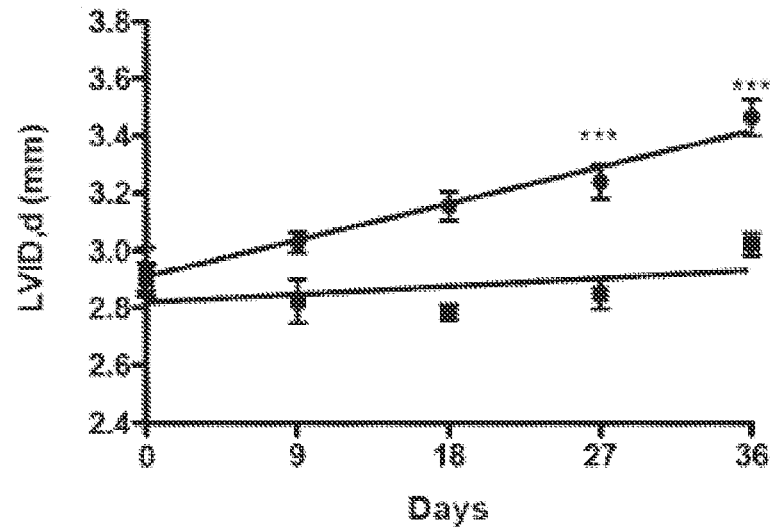
Figure 8D:
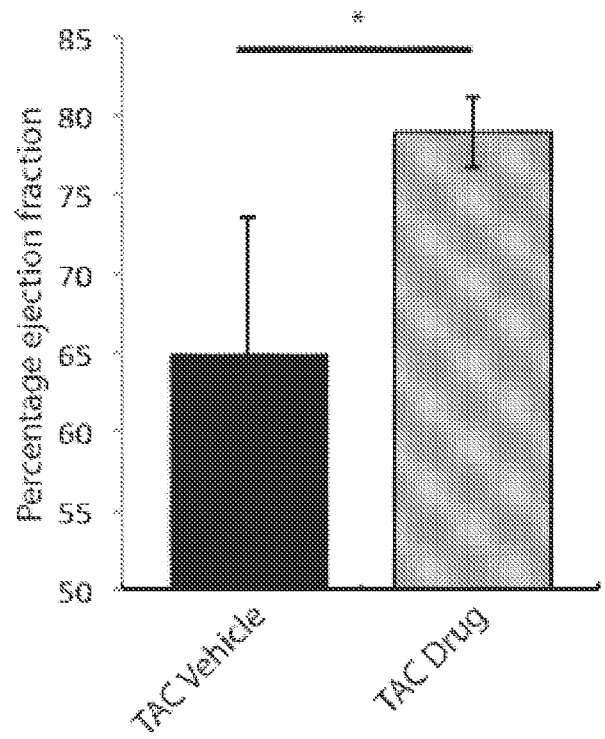
Figure 8E:
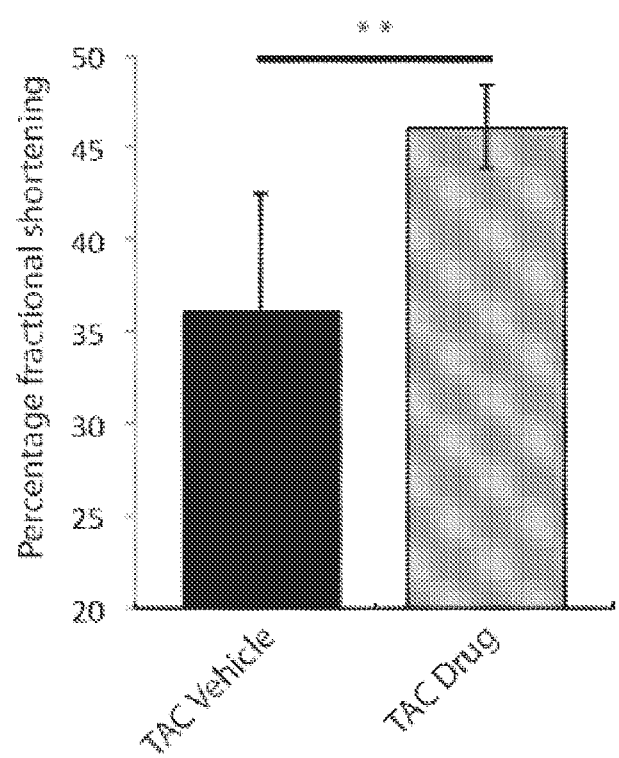

The mice were subjected to pressure overload induced cardiac hypertrophy by TAC while administered 4 mg/kg of BCTC (in 20% wt/vol 2-Hydroxypropyl)-β-cyclodextrin/PBS) throughout the entire experiment using osmotic pumps (Alzet, Model 2006) pumping continuously at a rate of 0.15 ul/hr. The test was limited to ~42 days (max) by the function of the pumps, as such the experiment was halted at 36 days post TAC, as pumps are installed previous to the TAC to allow recovery before the TAC surgery. Analysis of heart weights 36 days post TAC revealed that the heart weight/body weight ratio was significantly greater in vehicle treated WT mice than drug treated mice (p=0.035) (FIG. 8A). Echocardiographic assessment of mice every 9 days for the duration of the study showed that Vehicle and BCTC treated sham mice (Vehicle Sham (n=2) and BCTC sham mice (n=2)) show no difference in their left ventricular internal diameter (LVID,d) (FIG. 8B). However, BCTC treated TAC mice (n=8) have a significantly smaller LVIDd than the vehicle treated TAC mice (n=7) (FIG. 8C) from zero to thirty six days, indicating that the TAC Vehicle control mice start increasing their internal diameter at 9 days, whereas in TAC BCTC treated mice, the diameter is maintained for the duration of the test. The LVIDd is significantly different after 18 days (p<0.001). This protection from dilation of the left ventricle translates to a protection in the function of the heart as measured by ejection fraction (% EF, p<0.05) and fractional shortening (% FS). Both the % EF and % FS (p<0.01) of vehicle-treated TAC mice declined steadily over the course of the study and was significantly diminished at 36 days post TAC compared to drug-treated mice (FIGS. 8D, 8E).

Example 6

Figure 9A:
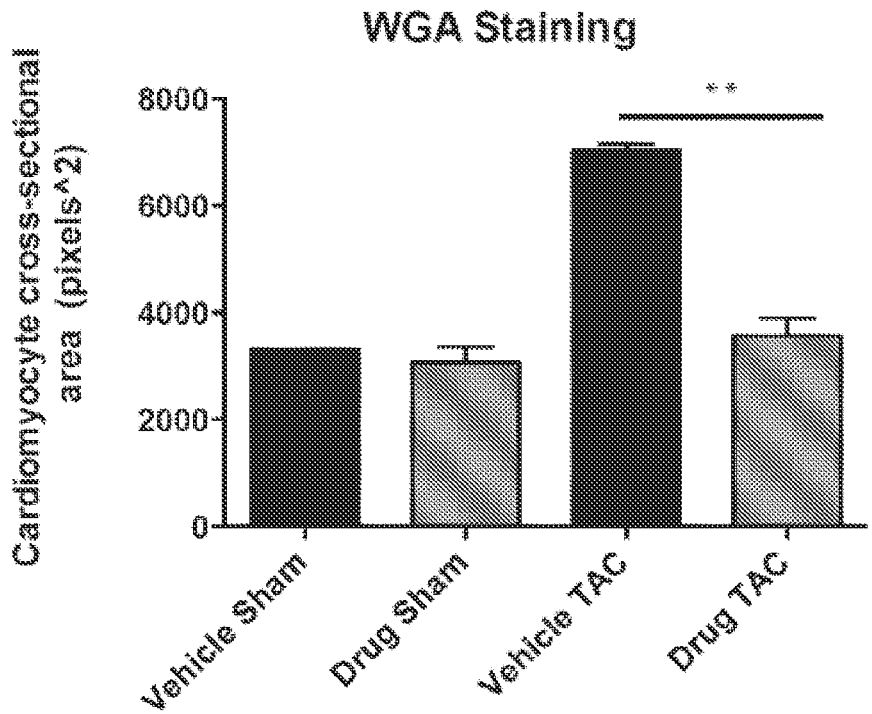
FIGS. 9A-9B are graphs of measurements from histological analysis of mice treated with the TRPV1 antagonist BCTC according to procedures described in Example 6.
Figure 9B:
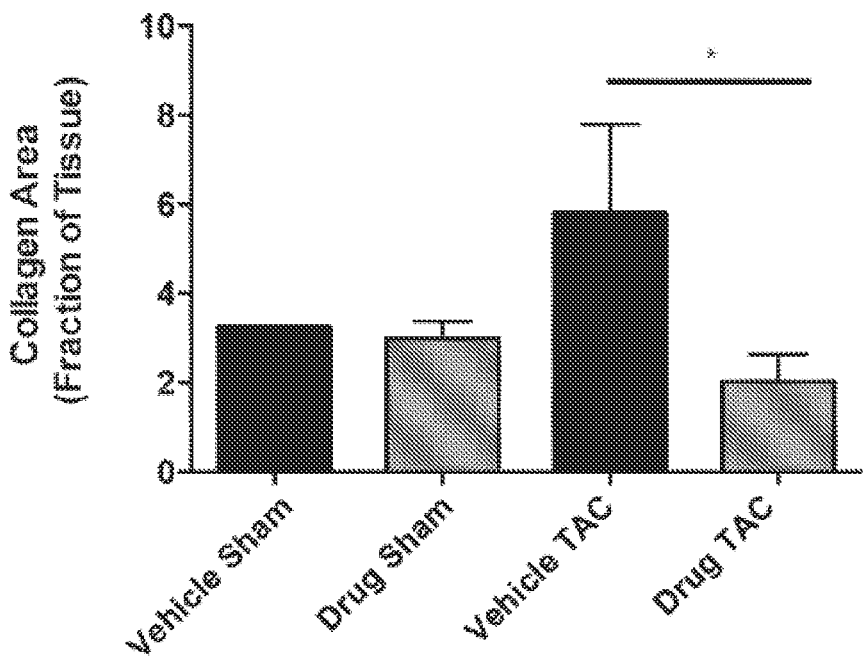

Mice Treated with the TRPV1 Antagonist BCTC Present Histologically with Less Hypertrophy and Fibrosis than Vehicle Control Mice, Thirty Six Days Post TAC Treatment Histological analysis of the heart 36 days post TAC shows that BCTC can protect the heart from cellular hypertrophy, and the deposition of interstitial fibrosis. From stains of plasma membranes (Wheat germ agglutinin-Alexa488) in heart tissue sections it is shown that BCTC treated TAC mice, described in Example 5, have smaller cardiac myocytes and less hypertrophy than vehicle treated TAC control mice. Measurement of cardiomyocyte cross sectional area shows significantly smaller myocytes in BCTC treated TAC mice than vehicle treated TAC control mice (p=<0.01, n=100) 36 days post TAC treatment (FIG. 9A), indicating that BCTC can protect the heart from hypertrophy at the cellular level. Less histological staining with Picrosirius red which can indicate areas of interstitial collagen deposition in isolated heart tissue sections from BCTC treated TAC mice than vehicle treated control mice indicates less interstitial collagen deposition. Analysis of collagen staining by ImageJ (NIH) was used to determine the area of collagen staining as a percentage of tissue area. The analysis (FIG. 9B) indicates that there is significantly less interstitial collagen in BCTC treated TAC mice than vehicle treated TAC control mice (p=0.05). This shows that BCTC can protect the heart from fibrosis during pressure overload cardiac hypertrophy.

CITATIONS

Lygate, C. 2006. Surgical models of hypertrophy and heart failure: Myocardial infarction and transverse aortic constriction. *Drug Discovery Today: Disease Models* 3:283-290.

Patten, R. D., and M. R. Hall-Porter. 2009. Small animal models of heart failure: development of novel therapies, past and present. *Circ Heart Fail* 2:138-144.

Rockman, H. A., S. Ono, R. S. Ross, L. R. Jones, M. Karimi, V. Bhargava, J. Ross, Jr., and K. R. Chien. 1994. Molecular and physiological alterations in murine ventricular dysfunction. *Proc Natl Acad Sci USA* 91:2694-2698.

Rockman, H. A., R. S. Ross, A. N. Harris, K. U. Knowlton, M. E. Steinhelper, L. J. Field, J. Ross, Jr., and K. R. Chien. 1991. Segregation of atrial-specific and inducible expression of an atrial natriuretic factor transgene in an in vivo murine model of cardiac hypertrophy. *Proc Natl Acad Sci USA* 88:8277-8281.

Caterina, M. J., et al. 2000. Impaired nociception and pain sensation in mice lacking the capsaicin receptor. *Science* 288:306-313.

Buckley, C. L., and Stokes, A. J. 2011. Mice lacking functional TRPV1 are protected from pressure overload cardiac hypertrophy. *Channels* 5:4, 1-8.

Shiojima, I., Sato, K., Izumiya, Y., Schiekofer, S., Ito, M., Liao, R., et al. 2005. Disruption of coordinated cardiac hypertrophy and angiogenesis contributes to the transition to heart failure. *J. Clin. Invest.* 115:2108-18.

Gunthrope, M. J., Rami, H. K., et al. 2004. Discovery of novel 6,6-heterocycles as transient receptor potential vanilloid (TRPV1) antagonists. *Neuropharmacol.* 46(1): 133-49.

Lin, Z., Reilly. C. A., et al. 2011. Nobilamides A-H, long-acting transient receptor potential vanilloid-1 (TRPV1) antagonists from mollusk-associated bacteria. *J. Med. Chem.* 54(11):3746-55.

Messeguer, A., Planells-Cases, R., et al. 2006. Physiology and pharmacology of the vanilloid receptor. *Curr. Neuropharmacol.* 4(1):1-15.

What is claimed is:

1. A method of reducing the plasma concentration of a marker of cardiac hypertrophy in a mammalian subject with cardiac hypertrophy comprising administering to the subject an anti-hypertrophic effective amount of an ion channel TRPV1 inhibitor.

2. The method according to claim 1 wherein the marker of cardiac hypertrophy is atrial natriuretic peptide (ANP), TGFβ, MMP2, CMA1, or a combination thereof.

3. The method according to claim 2 wherein the marker of cardiac hypertrophy is atrial natriuretic peptide (ANP).

4. The method according to claim 2 wherein the marker of cardiac hypertrophy is TGFβ.

5. The method according to claim 2 wherein the marker of cardiac hypertrophy is MMP2.

6. The method according to claim 2 wherein the marker of cardiac hypertrophy is CMA1.

7. The method according to claim 1 wherein the ion channel TRPV1 inhibitor is selected from the group consisting of:
N-(4-tertiarybutylphenyl)-4-(3-chloropyridin-2-yl)-tetrahydropyrazine-1(2H)-carboxamide;
N-(3-Methoxyphenyl)-4-chlorocinnamide;
1-lsoquinolin-5-yl-3-(4-trifluoromethyl-benzyl)-urea;
(2E)-N-(2,3-Dihydro-1,4-benzodioxin-6-yl)-3-[4-(1,1-dimethylethyl) phenyl]-2-propenamide;
2-Acetylamino-4-[6'-(4-trifluoromethylphenyl)-pyrimidin-4'-yl-oxy]-benzothiazole;
N-(2-bromophenyl-N'-[((R)-1-(5-trifluoromethyl-2-pyridyl) pyrrolidin-3-yl)]urea;
N-(2-bromophenyl)-N'-{2-[ethyl (3-methylphenyl) amino]ethyl}urea;
(R)-(5-tert-butyl-2,3-dihydro-1H-inden-1-yl)-3-(1H-indazol-4-yl)-urea;
N-(Isoquinolin-5-yl)-N'-[spiro-(cyclobutane-1,2'-(3',4'-dihydro-benzopyran-4'-yl))]urea;
(2R)-4-(3-chloro-2-pyridinyl)-2-methyl-N-[4-(trifluoromethyl) phenyl]-1-piperazinecarboxamide;
4-(4'-Trifluoromethyl-anilino)-7-(3'-trifluoromethyl-pyridin-2-yl)-quinazoline;
N-[2-(4-chlorophenyl)ethyl]-1,3,4,5-tetrahydro-7,8-dihydroxy-2H-2-benzazepine-2-carbothioamide;
(5R*,8R*,6E,9E)-5,8-Dimethyl-4-methylenetetradeca-6,9-dienoic acid;
1-(3-Fluorobenzyl)-2-(N-(1,2-dimethyl-1,3-isoindazol-5-yl)-acetamido)-{pyridine-[3,4-b]-pyrrole};
N-(4-chlorobenzyl)-N'-(1-methyl-1H-indazol-4-yl)urea;
N-(4-tert-butylbenzyl)-N'-(1-methyl-1H-indazol-4-yl) urea;
N-(3-fluoro-4-(trifluoromethyl)benzyl)-N'-(1-methyl-1H-indazol-4-yl)-urea;
N-(4-fluoro-3-(trifluoromethyl)benzyl)-N'-(1-methyl-1H-indazol-4-yl)-urea;
N-(3,4-dichlorobenzyl)-N'-(1-methyl-1H-indazol-4-yl) urea;
N-(2,4-dichlorobenzyl)-N'-(1-methyl-1H-indazol-4-yl) urea;
N-(4-ethylbenzyl)-N'-(1-methyl-1H-indazol-4-yl)urea;
N-(2-chlorobenzyl)-N'-(1-methyl-1H-indazol-4-yl)urea;
N-(4-fluorobenzyl)-N'-(1-methyl-1H-indazol-4-yl)urea;
N-(2-fluorobenzyl)-N'-(1-methyl-1H-indazol-4-yl)urea;
N-[1-(bromophenyl)ethyl-N'-(1-methyl-1H-Indazol-4-yl) urea;
N-(1-methyl-1H-indazol-4-yl)-N'-{4-[(trifluoromethyl) thio]benzyl}urea;
1-(2,3-dichlorophenyl)-3-[2-(N-ethyl-3-methylanilino) ethyl]urea;
1-[2-(N-ethyl-3-methylanilino)ethyl]-3-naphthalen-1-ylurea;
1-(4-bromophenyl)-3-[2-(N-ethyl-3-methylanilino)ethyl] urea;
1-(3-bromophenyl)-3-[2-(N-ethyl-3-methylanilino)ethyl] urea;
1-(chlorophenyl)-3-[2-(N-ethyl-3-methylanilino)ethyl] urea;
1-[2-(N-ethyl-3-methylanilino)ethyl]-3-(2-fluorophenyl) urea;
1-[2-{N-ethyl-3-methylanilino)ethyl]-3-(2-methylphenyl)urea;
1-[2-(N-ethyl-3-methylanilino)ethyl]-3-phenylurea;
2-[(2-bromophenyl)carbamoylamino]ethyl-ethylmethyl-(3-methylphenyl) azanium iodide;
1-(2-bromophenyl)-3-[2-(N-ethyl-3-fluoro-4-methylanilino)ethyl]urea;

1-(2-bromophenyl)-3-[2-(N-ethyl-3,4-difluoroanilino) ethyl]urea;
1-(2-bromophenyl)-3-[2-(N-ethyl-3-fluoroanilino)ethyl] urea;
1-(2-bromophenyl)-3-[2-(N-ethyl-4-methylanilino)ethyl] urea;
1-(2-bromophenyl)-3-[2-(N-ethyl-2-methylanilino)ethyl] urea;
1-(2-bromophenyl)-3-[2-(N-ethylanilino)ethyl]urea;
N-[2-[(2-bromophenyl)carbamoylamino]ethyl]-N-(3-methylphenyl)acetamide;
1-[2-{N-benzyl-3-methylanilino)ethyl]-3-(2-bromophenyl)urea;
1-(2-bromophenyl)-3-[2-(2,3-dimethylanilino)ethyl]urea;
1-(2-bromophenyl)-3-[2-(3-methylanilino)ethyl]urea;
1-(2,5-dichlorophenyl)-3-[2-(N-ethyl-3-methylanilino) ethyl]urea;
4-fluoro-4-(3-methylpyridin-2-yl)-N-[4-trifluoromethylphenyl]piperidine-1-carboxamide;
4-fluoro-4 (pyridin-2-yl)N-[4-trifluoromethylphenyl]piperidine-1-carboxamide;
4-fluoro-4 (pyridine-2-yl)N-[4-trifluoromethylbenzyl]piperidine-1-carboxamide;
2-{4-fluoro-1-[4-trifluoromethylbenzoyl]piperidin-4-yl}pyridine;
2-(4-fluoro-1-{[4-trifluoromethylphenyl] acetyl}piperidin-4-yl) pyridine;
2-(4-fluoro-1-{3-[4-trifluoromethylphenyl] propanoyl}piperidin-4-yl) pyridine;
4-fluoro-4-(1-methyl-1H-imidazol-2-yl)-N-[4-trifluoromethylphenyl]piperidine-1-carboxamide;
4-methoxy-4-pyridin-2-yl-N-[4-trifluoromethylphenyl] piperidine-1-carboxamide;
4-methoxy-4-pyridin-2-yl-N-[4-trifluoromethylbenzyl] piperidine-1-carboxamide;
4-fluoro-N-(4-isopropylphenyl)-4-(3-methylpyridin-2-yl) piperidine-1-carboxamide;
4-fluoro-4-(3-methylpyridin-2-yl)-N-{4-[1,2,2,2-tetrafluoro-1-trifluoromethylethyl]phenyl}piperidine-1-carboxamide;
N-(4-Tert-butylphenyl)-4-fluoro-4-(3-methylpyridin-2-yl) piperidine-1-carboxamide;
4-fluoro-4-(3-methylpyridin-2-yl)-N-[4-(pentafluoro-lambda (sup 6)-sulfanyl) phenyl]piperidine-1-carboxamide;
N-(4-Butylphenyl)-4-fluoro-4-(3-methylpyridin-2-yl) piperidine-1-carboxamide;
N-(4-Benzylphenyl)-4-fluoro-4-(3-methylpyridin-2-yl) piperidine-1-carboxamide;
N-biphenyl-4-yl-4-fluoro-4-(3-methylpyridin-2-yl) piperidine-1-carboxamide;
4-fluoro-4-(3-methylpyridin-2-yl)-N-[5-trifluoromethylpyridin-2-yl]piperidine-1-carboxamide;
4-(3-chloropyridin-2-yl)-4-fluoro-N-[4-trifluoromethylphenyl]piperidine-1-carboxamide;
4-fluoro-4-(3-fluoropyridin-2-yl)-N-[4-trifluoromethylphenyl]piperidine-1-carboxamide;
4-fluoro-4-(3-methoxypyridin-2-yl)-N-[4-trifluoromethylphenyl]piperidine-1-carboxamide;
4-fluoro-4-(3-methylpyridin-2-yl)-N-[4-trifluoromethylphenyl]piperidine-1-carbothioamide;
N'-cyano-4-fluoro-4-(3-methylpyridin-2-yl)-N-[4-trifluoromethylphenyl]piperidine-1-carboximidamide;
4-fluoro-4-(3-methylpyridin-2-yl)-N'-(1-phenylpiperidin-4-yl)-N-[4-trifluoromethylphenyl]piperidine-1-carboximidamide;
4-fluoro-4-phenyl-N-[4-trifluoromethylphenyl]piperidine-1-carboxamide;
(+/−)-(syn)-4-fluoro-2-methyl-4-(3-methylpyridin-2-yl)-N-[4-trifluoromethylphenyl] piperidine-1-carboxamide;
4-(fluoromethyl)-4-pyridin-2-yl-N-[4-trifluoromethylphenyl]piperidine-1-carboxamide;
syn- and anti-3-fluoro-3-pyridin-2-yl-N-[4-trifluoromethylphenyl]-8-azabicyclo[3.2.1]octane-8-carboxamide;
3-fluoro-3-pyridin-2-yl-N-[4-trifluoromethylphenyl]-8-azabicyclo[3.2.1]octane-8-carboxamide;
4-fluoro-4-pyrimidin-2-yl-N-[4-trifluoromethylphenyl] piperidine-1-carboxamide;
4-fluoro-4-(3-phenylpropyl)-N-[4-trifluoromethylphenyl] piperidine-1-carboxamide;
2-[4-fluoro-4-(3-methylpyridin-2-yl) piperidin-1-yl]-6-trifluoromethyl-1H-benzimidazole;
2-(4-fluoro-4-pyridin-2-ylpiperidin-1-yl)-6-(trifluoromethyl)-1H-benzimidazole;
4-fluoro-N-[4-trifluoromethylphenyl]-4-[3-trifluoromethylpyridin-2-yl]piperidine-1-carboxamide;
4-fluoro-N-(4-methylphenyl)-4-(3-methylpyridin-2-yl) piperidine-1-carboxamide;
N-(4-ethylphenyl)-4-fluoro-4-(3-methylpyridin-2-yl) piperidine-1-carboxamide;
N-(4-chlorophenyl)-4-fluoro-4-(3-methylpyridin-2-yl) piperidine-1-carboxamide;
4-fluoro-4-(3-methylpyridin-2-yl)-N-[4-trifluoromethoxyphenyl]piperidine-1-carboxamide;
N-(4-cyanophenyl)-4-fluoro-4-(3-methylpyridin-2-yl) piperidine-1-carboxamide;
N-[4-dimethylaminophenyl]-4-fluoro-4-(3-methylpyridin-2-yl) piperidine-1-carboxamide;
1-(2-(3,3-dimethylbutyl)-4-(trifluoromethyl)benzyl)-3-(1-methyl-1H-indazo-1-4-yl)urea;
N-acetyl-1-phenylalanyl-l-leucinamide;
and pharmaceutically acceptable salts thereof.

8. The method according to claim 1 wherein the inhibitor comprises N-(4-t-butyl-phenyl)-4-(3-chloropyridin-2-yl)-tetrahydropyrazine-1(2H)-carboxamide or a pharmaceutically acceptable salt thereof.

9. A method of reducing the plasma concentration of atrial natriuretic peptide (ANP) in a mammalian subject with cardiac hypertrophy comprising administering to the subject an anti-hypertrophic effective amount of an ion channel TRPV1 inhibitor.

10. The method according to claim 9 wherein the ion channel TRPV1 inhibitor is selected from the group consisting of:
N-(4-tertiarybutylphenyl)-4-(3-chloropyridin-2-yl)-tetrahydropyrazine-1(2H)-carboxamide;
N-(3-Methoxyphenyl)-4-chlorocinnamide;
1-Isoquinolin-5-yl-3-(4-trifluoromethyl-benzyl)-urea;
(2E)-N-(2,3-Dihydro-1,4-benzodioxin-6-yl)-3-[4-(1,1-dimethylethyl) phenyl]-2-propenamide;
2-Acetylamino-4-[6'-(4-trifluoromethylphenyl)-pyrimidin-4'-yl-oxy]-benzothiazole;
N-(2-bromophenyl-N'-[((R)-1-(5-trifluoromethyl-2-pyridyl) pyrrolidin-3-yl)]urea;
N-(2-bromophenyl)-N'-{2-[ethyl (3-methylphenyl) amino]ethyl}urea;
(R)-(5-tert-butyl-2,3-dihydro-1H-inden-1-yl)-3-(1H-indazol-4-yl)-urea;
N-(Isoquinolin-5-yl)-N'-[spiro-(cyclobutane-1,2'-(3',4'-dihydro-benzopyran-4'-yl))]urea;
(2R)-4-(3-chloro-2-pyridinyl)-2-methyl-N-[4-(trifluoromethyl) phenyl]-1-piperazinecarboxamide;

4-(4'-Trifluoromethyl-anilino)-7-(3'-trifluoromethyl-pyridin-2-yl)-quinazoline;
N-[2-(4-chlorophenyl)ethyl]-1,3,4,5-tetrahydro-7,8-dihydroxy-2H-2-benzazepine-2-carbothioamide;
(5R*,8R*,6E,9E)-5,8-Dimethyl-4-methylenetetradeca-6,9-dienoic acid;
1-(3-Fluorobenzyl)-2-(N-(1,2-dimethyl-1,3-isoindazol-5-yl)-acetamido)-{pyridine-[3,4-b]-pyrrole};
N-(4-chlorobenzyl)-N'-(1-methyl-1H-indazol-4-yl)urea;
N-(4-tert-butylbenzyl)-N'-(1-methyl-1H-indazol-4-yl) urea;
N-(3-fluoro-4-(trifluoromethyl)benzyl)-N'-(1-methyl-1H-indazol-4-yl)-urea;
N-(4-fluoro-3-(trifluoromethyl)benzyl)-N'-(1-methyl-1H-indazol-4-yl)-urea;
N-(3,4-dichlorobenzyl)-N'-(1-methyl-1H-indazol-4-yl) urea;
N-(2,4-dichlorobenzyl)-N'-(1-methyl-1H-indazol-4-yl) urea;
N-(4-ethylbenzyl)-N'-(1-methyl-1H-indazol-4-yl)urea;
N-(2-chlorobenzyl)-N'-(1-methyl-1H-indazol-4-yl)urea;
N-(4-fluorobenzyl)-N'-(1-methyl-1H-indazol-4-yl)urea;
N-(2-fluorobenzyl)-N'-(1-methyl-1H-indazol-4-yl)urea;
N-[1-(bromophenyl)ethyl-N'-(1-methyl-1H-Indazol-4-yl) urea;
N-(1-methyl-1H-indazol-4-yl)-N'-{4-[(trifluoromethyl) thio]benzyl}urea;
1-(2,3-dichlorophenyl)-3-[2-(N-ethyl-3-methylanilino) ethyl]urea;
1-[2-(N-ethyl-3-methylanilino)ethyl]-3-naphthalen-1-ylurea;
1-(4-bromophenyl)-3-[2-(N-ethyl-3-methylanilino)ethyl] urea;
1-(3-bromophenyl)-3-[2-(N-ethyl-3-methylanilino)ethyl] urea;
1-(chlorophenyl)-3-[2-(N-ethyl-3-methylanilino)ethyl] urea;
1-[2-(N-ethyl-3-methylanilino)ethyl]-3-(2-fluorophenyl) urea;
1-[2-{N-ethyl-3-methylanilino)ethyl]-3-(2-methylphenyl)urea;
1-[2-(N-ethyl-3-methylanilino)ethyl]-3-phenylurea;
2-[(2-bromophenyl)carbamoylamino]ethyl-ethylmethyl-(3-methylphenyl) azanium iodide;
1-(2-bromophenyl)-3-[2-(N-ethyl-3-fluoro-4-methylanilino)ethyl]urea;
1-(2-bromophenyl)-3-[2-(N-ethyl-3,4-difluoroanilino) ethyl]urea;
1-(2-bromophenyl)-3-[2-(N-ethyl-3-fluoroanilino)ethyl] urea;
1-(2-bromophenyl)-3-[2-(N-ethyl-4-methylanilino)ethyl] urea;
1-(2-bromophenyl)-3-[2-(N-ethyl-2-methylanilino)ethyl] urea;
1-(2-bromophenyl)-3-[2-(N-ethylanilino)ethyl]urea;
N-[2-[(2-bromophenyl)carbamoylamino]ethyl]-N-(3-methylphenyl)acetamide;
1-[2-{N-benzyl-3-methylanilino)ethyl]-3-(2-bromophenyl)urea;
1-(2-bromophenyl)-3-[2-(2,3-dimethylanilino)ethyl]urea;
1-(2-bromophenyl)-3-[2-(3-methylanilino)ethyl]urea;
1-(2,5-dichlorophenyl)-3-[2-(N-ethyl-3-methylanilino) ethyl]urea;
4-fluoro-4-(3-methylpyridin-2-yl)-N-[4-trifluoromethylphenyl]piperidine-1-carboxamide;
4-fluoro-4 (pyridin-2-yl)N-[4-trifluoromethylphenyl]piperidine-1-carboxamide;
4-fluoro-4 (pyridine-2-yl)N-[4-trifluoromethylbenzyl]piperidine-1-carboxamide;
2-{4-fluoro-1-[4-trifluoromethylbenzoyl]piperidin-4-yl}pyridine;
2-(4-fluoro-1-{[4-trifluoromethylphenyl] acetyl}piperidin-4-yl) pyridine;
2-(4-fluoro-1-{3-[4-trifluoromethylphenyl] propanoyl}piperidin-4-yl) pyridine;
4-fluoro-4-(1-methyl-1H-imidazol-2-yl)-N-[4-trifluoromethylphenyl]piperidine-1-carboxamide;
4-methoxy-4-pyridin-2-yl-N-[4-trifluoromethylphenyl] piperidine-1-carboxamide;
4-methoxy-4-pyridin-2-yl-N-[4-trifluoromethylbenzyl] piperidine-1-carboxamide;
4-fluoro-N-(4-isopropylphenyl)-4-(3-methylpyridin-2-yl) piperidine-1-carboxamide;
4-fluoro-4-(3-methylpyridin-2-yl)-N-{4-[1,2,2,2-tetrafluoro-1-trifluoromethylethyl]phenyl}piperidine-1-carboxamide;
N-(4-Tert-butylphenyl)-4-fluoro-4-(3-methylpyridin-2-yl) piperidine-1-carboxamide;
4-fluoro-4-(3-methylpyridin-2-yl)-N-[4-(pentafluoro-lambda (sup 6)-sulfanyl) phenyl]piperidine-1-carboxamide;
N-(4-Butylphenyl)-4-fluoro-4-(3-methylpyridin-2-yl) piperidine-1-carboxamide;
N-(4-Benzylphenyl)-4-fluoro-4-(3-methylpyridin-2-yl) piperidine-1-carboxamide;
N-biphenyl-4-yl-4-fluoro-4-(3-methylpyridin-2-yl) piperidine-1-carboxamide;
4-fluoro-4-(3-methylpyridin-2-yl)-N-[5-trifluoromethylpyridin-2-yl]piperidine-1-carboxamide;
4-(3-chloropyridin-2-yl)-4-fluoro-N-[4-trifluoromethylphenyl]piperidine-1-carboxamide;
4-fluoro-4-(3-fluoropyridin-2-yl)-N-[4-trifluoromethylphenyl]piperidine-1-carboxamide;
4-fluoro-4-(3-methoxypyridin-2-yl)-N-[4-trifluoromethylphenyl]piperidine-1-carboxamide;
4-fluoro-4-(3-methylpyridin-2-yl)-N-[4-trifluoromethylphenyl]piperidine-1-carbothioamide;
N'-cyano-4-fluoro-4-(3-methylpyridin-2-yl)-N-[4-trifluoromethylphenyl]piperidine-1-carboximidamide;
4-fluoro-4-(3-methylpyridin-2-yl)-N'-(1-phenylpiperidin-4-yl)-N-[4-trifluoromethylphenyl]piperidine-1-carboximidamide;
4-fluoro-4-phenyl-N-[4-trifluoromethylphenyl]piperidine-1-carboxamide;
(+/−)-(syn)-4-fluoro-2-methyl-4-(3-methylpyridin-2-yl)-N-[4-trifluoromethylphenyl]piperidine-1-carboxamide;
4-(fluoromethyl)-4-pyridin-2-yl-N-[4-trifluoromethylphenyl]piperidine-1-carboxamide;
syn- and anti-3-fluoro-3-pyridin-2-yl-N-[4-trifluoromethylphenyl]-8-azabicyclo[3.2.1]octane-8-carboxamide;
3-fluoro-3-pyridin-2-yl-N-[4-trifluoromethylphenyl]-8-azabicyclo[3.2.1]octane-8-carboxamide;
4-fluoro-4-pyrimidin-2-yl-N-[4-trifluoromethylphenyl] piperidine-1-carboxamide;
4-fluoro-4-(3-phenylpropyl)-N-[4-trifluoromethylphenyl] piperidine-1-carboxamide;
2-[4-fluoro-4-(3-methylpyridin-2-yl) piperidin-1-yl]-6-trifluoromethyl-1H-benzimidazole;
2-(4-fluoro-4-pyridin-2-ylpiperidin-1-yl)-6-(trifluoromethyl)-1H-benzimidazole;
4-fluoro-N-[4-trifluoromethylphenyl]-4-[3-trifluoromethylpyridin-2-yl]piperidine-1-carboxamide;
4-fluoro-N-(4-methylphenyl)-4-(3-methylpyridin-2-yl) piperidine-1-carboxamide;

N-(4-ethylphenyl)-4-fluoro-4-(3-methylpyridin-2-yl) piperidine-1-carboxamide;
N-(4-chlorophenyl)-4-fluoro-4-(3-methylpyridin-2-yl) piperidine-1-carboxamide;
4-fluoro-4-(3-methylpyridin-2-yl)-N-[4-trifluoromethoxyphenyl]piperidine-1-carboxamide;
N-(4-cyanophenyl)-4-fluoro-4-(3-methylpyridin-2-yl) piperidine-1-carboxamide;
N-[4-dimethylaminophenyl]-4-fluoro-4-(3-methylpyridin-2-yl) piperidine-1-carboxamide;
1-(2-(3,3-dimethylbutyl)-4-(trifluoromethyl)benzyl)-3-(1-methyl-1H-indazo-1-4-yl)urea;
N-acetyl-1-phenylalanyl-l-leucinamide;
and pharmaceutically acceptable salts thereof.

11. The method according to claim 9 wherein the ion channel TRPV1 inhibitor comprises N-(4-t-butyl-phenyl)-4-(3-chloropyridin-2-yl)-tetrahydropyrazine-1(2H)-carboxamide or a pharmaceutically acceptable salt thereof.

* * * * *

UNITED STATES PATENT AND TRADEMARK OFFICE
CERTIFICATE OF CORRECTION

PATENT NO. : 12,403,139 B2
APPLICATION NO. : 18/243572
DATED : September 2, 2025
INVENTOR(S) : Alexander Stokes It is certified that error appears in the above-identified patent and that said Letters Patent is hereby corrected as shown below:

On the Title Page

Column 1, Line 1, delete "(60)" and insert --(63)--.

On Page 2, item [56], Column 1, Line 19, delete "A. "Ion channels"" and insert --A. "Ion channels--.

In the Specification

In Column 4, Line 49, delete "Porter, 2009)" and insert --Porter, 2009).--.

In Column 4, Line 67, delete "with isofluorene gas" and insert --with isoflurane gas--.

In Column 5, Line 42, delete "cell CD161$^{(RT,WB,H)}$"" and insert --cell CD161$^{(RT,WB,H)}$.--.

In Column 6, Line 54, delete "Calbiochem, CB1001). The" and insert --Calbiochem, CB1001). The--.

In Column 7, Line 28, delete "1-lsoquinolin-5-yl" and insert --1-Isoquinolin-5-yl--.

In Column 7, Line 48, delete "Carbothioamide (Capsazapine)" and insert --carbothioamide (Capsazepine)--.

In Column 9, Line 55, delete "succinates, palmoates, methanesulphonates" and insert --succinates, pamoates, methanesulphonates--.

In Column 11, Line 35, delete "in unanethestized mice" and insert --in unanesthetized mice--.

In Column 11, Lines 47, 51, 54, 56, delete "in C57BU6" and insert --in C57BL/6.--.

Signed and Sealed this
Tenth Day of February, 2026

John A. Squires
*Director of the United States Patent and Trademark Office*

CERTIFICATE OF CORRECTION (continued)
U.S. Pat. No. 12,403,139 B2

In Column 11, Line 63 (Approx ), delete "fractional shortening" and insert --fractional shortening.--.

In Column 12, Line 12, delete "in C57BU6" and insert --in C57BL/6.--.

In Column 12, Line 50 (Approx.), delete "4A, 4B)" and insert --4A, 4B).--.

In Column 12, Line 52, delete "(p<0.05)." and insert --(p<0.05),--.

In Column 13, Line 13, delete "sing unanesthestized transthoracic" and insert --using unanesthetized transthoracic--.

In Column 15, Line 29, delete "WT TAC compared" and insert --WT TAC mice compared--.

In Column 15, Line 35, delete "cell chymase. CMA1," and insert --cell chymase, CMA1,--.

In Column 15, Lines 45-46, delete "and Chymasc protein" and insert --and Chymase protein--.

In Column 17, Line 43, delete "Z., Reilly. C." and insert --Z., Reilly, C.--.

In the Claims

In Column 18, Claim 7, Line 7, delete "1-lsoquinolin-5" and insert --1-Isoquinolin-5--.

In Column 18, Claim 7, Lines 8-9, delete "1,1-dimethylethyl) phenyl]-2" and insert --1, 1-dimethylethyl)phenyl]-2--.

In Column 18, Claim 7, Line 13, delete "2-pyridyl) pyrrolidin-3-" and insert --2-pyridyl)pyrrolidin-3- --.

In Column 18, Claim 7, Line 14, delete "-[ethyl (3-methylphenyl)" and insert -- -[ethyl(3-methylphenyl)--.

In Column 18, Claim 7, Line 21, delete "trifluoromethyl) phenyl]-1-" and insert --trifluoromethyl)phenyl]-1- --.

In Column 18, Claim 7, Line 65, delete "(3-methylphenyl) azanium iodide;" and insert --(3-methylphenyl)azanium iodide;--.

In Column 19, Claim 7, Line 21, delete "fluoro-4 (pyridin" and insert --fluoro-4(pyridin--.

In Column 19, Claim 7, Line 23, delete "fluoro-4 (pyridine-2-" and insert --fluoro-4(pyridine-2- --.

In Column 19, Claim 7, Line 28, delete "4-yl) pyridine;" and insert --4-yl)pyridine;--.

CERTIFICATE OF CORRECTION (continued)
U.S. Pat. No. 12,403,139 B2

In Column 19, Claim 7, Line 43, delete "2-yl) piperidine-1" and insert --2-yl)piperidine-1--.

In Column 19, Claim 7, Line 45, delete "pentafluoro-lambda (sup 6)" and insert --pentafluoro-lambda(sup 6)--.

In Column 20, Claim 7, Line 4, delete "N-[4-trifluoromethylphenyl] piperidine-1" and insert --N-[4-trifluoromethylphenyl]piperidine-1--.

In Column 20, Claim 7, Line 16, delete "2-yl) piperidin-1" and insert --2-yl)piperidin-1--.

In Column 20, Claim 7, Lines 24-25, delete "2-yl) piperidine- 1" and insert --2-yl)piperidine- 1--.

In Column 20, Claim 7, Line 33, delete "2-yl) piperidine- 1" and insert --2-yl)piperidine- 1--.

In Column 20, Claim 10, Line 53, delete "1-lsoquinolin-5" and insert --1-Isoquinolin-5--.

In Column 20, Claim 10, Lines 54-55, delete "1,1-dimethylethyl) phenyl]-2" and insert --1,1-dimethylethyl)phenyl]-2--.

In Column 20, Claim 10, Line 59, delete "2-pyridyl) pyrrolidin-3-" and insert --2-pyridyl)pyrrolidin-3- --.

In Column 20, Claim 10, Line 60, delete "-[ethyl (3-methylphenyl)" and insert -- -[ethyl(3-methylphenyl)--.

In Column 20, Claim 10, Line 67, delete "trifluoromethyl) phenyl]-1-" and insert --trifluoromethyl)phenyl]-1- --.

In Column 21, Claim 10, Line 44, delete "(3-methylphenyl) azanium iodide;" and insert --(3-methylphenyl)azanium iodide;--.

In Column 21, Claim 10, Line 66, delete "fluoro-4 (pyridin-2" and insert --fluoro-4(pyridin-2--.

In Column 22, Claim 10, Line 1, delete "fluoro-4 (pyridine-2" and insert --fluoro-4(pyridine-2--.

In Column 22, Claim 10, Line 6, delete "4-yl) pyridine;" and insert --4-yl)pyridine;--.

In Column 22, Claim 10, Line 8, delete "4-yl) pyridine;" and insert --4-yl)pyridine;--.

In Column 22, Claim 10, Line 21, delete "2-yl) piperidine-1" and insert --2-yl)piperidine-1--.

In Column 22, Claim 10, Line 23, delete "pentafluoro-lambda (sup 6)" and insert --pentafluoro-lambda(sup 6)--.

CERTIFICATE OF CORRECTION (continued)
U.S. Pat. No. 12,403,139 B2

In Column 22, Claim 10, Line 60, delete "2-yl) piperidin-1" and insert --2-yl)piperidin-1--.

In Column 23, Claim 10, Lines 1-2, delete "2-yl) piperidine- 1" and insert --2-yl)piperidine- 1--.

In Column 23, Claim 10, Line 10, delete "2-yl) piperidine- 1" and insert --2-yl)piperidine- 1--.